(12) United States Patent
Akeson et al.

(10) Patent No.: US 7,238,485 B2
(45) Date of Patent: Jul. 3, 2007

(54) METHODS AND APPARATUS FOR CHARACTERIZING POLYNUCLEOTIDES

(75) Inventors: Mark Akeson, Santa Cruz, CA (US); Daniel Branton, Lexington, MA (US); David W. Deamer, Santa Cruz, CA (US); Jeffrey R. Sampson, San Francisco, CA (US)

(73) Assignees: President and Fellows of Harvard College, Cambridge, MA (US); Regents of the University of California, Oakland, CA (US); Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 11/088,140

(22) Filed: Mar. 23, 2005

(65) Prior Publication Data

US 2006/0063171 A1    Mar. 23, 2006

Related U.S. Application Data

(60) Provisional application No. 60/555,665, filed on Mar. 23, 2004.

(51) Int. Cl.
| | | |
|---|---|---|
| C12Q 1/68 | (2006.01) | |
| C12M 1/00 | (2006.01) | |
| C07H 21/02 | (2006.01) | |
| C07H 21/04 | (2006.01) | |

(52) U.S. Cl. .................. 435/6; 435/283.1; 536/23.1; 536/24.3

(58) Field of Classification Search ............. 435/6, 435/283.1; 536/23.1, 24.3
See application file for complete search history.

(56) References Cited

U.S. PATENT DOCUMENTS

| | | |
|---|---|---|
| 3,856,633 A | 12/1974 | Fletcher, III |
| 4,456,522 A | 6/1984 | Blackburn |
| 4,521,729 A | 6/1985 | Kiesewetter et al. |
| H201 H | 1/1987 | Yager |
| 4,661,235 A | 4/1987 | Krull et al. |
| 4,874,499 A | 10/1989 | Smith et al. |
| 5,001,048 A | 3/1991 | Taylor et al. |
| 5,111,221 A | 5/1992 | Fare et al. |
| 5,221,447 A | 6/1993 | Hjerten |
| 5,234,566 A | 8/1993 | Osman et al. |
| 5,356,776 A | 10/1994 | Kambara et al. |
| 5,376,878 A | 12/1994 | Fisher |
| 5,378,342 A | 1/1995 | Ikematsu et al. |
| 5,503,744 A | 4/1996 | Ikematsu et al. |
| 5,612,179 A | 3/1997 | Simons |
| 5,795,782 A | 8/1998 | Church et al. |
| 5,833,826 A | 11/1998 | Nordman |
| 5,911,871 A | 6/1999 | Preiss et al. |
| 6,015,714 A | 1/2000 | Baldarelli et al. |
| 6,054,035 A | 4/2000 | Kambara |
| 6,156,502 A | 12/2000 | Beattie |
| 6,190,865 B1 | 2/2001 | Jendrisak et al. |
| 6,203,993 B1 | 3/2001 | Shuber et al. |
| 6,214,545 B1 | 4/2001 | Dong et al. |
| 6,221,603 B1 | 4/2001 | Mahtani |
| 6,238,866 B1 | 5/2001 | Yeh et al. |
| 6,263,286 B1 * | 7/2001 | Gilmanshin et al. .......... 702/19 |
| 6,267,872 B1 | 7/2001 | Akeson et al. |
| 6,355,420 B1 | 3/2002 | Chan |
| 6,362,002 B1 | 3/2002 | Denison |
| 6,403,311 B1 | 6/2002 | Chan |
| 6,464,842 B1 | 10/2002 | Golovchenko et al. |
| 6,503,409 B1 * | 1/2003 | Fleming ...................... 216/56 |
| 6,528,258 B1 | 3/2003 | Russell |
| 6,627,067 B1 | 9/2003 | Branton et al. |
| 6,673,615 B2 | 1/2004 | Denison et al. |
| 6,746,594 B2 | 6/2004 | Akeson et al. |
| 6,783,643 B2 | 8/2004 | Golovchenko et al. |
| 2002/0039737 A1 | 4/2002 | Chan et al. |
| 2002/0081744 A1 | 6/2002 | Chan et al. |
| 2002/0119455 A1 | 8/2002 | Chan et al. |
| 2003/0044816 A1 | 3/2003 | Denison et al. |
| 2003/0059822 A1 | 3/2003 | Chan et al. |
| 2003/0066749 A1 | 4/2003 | Golovchenko et al. |
| 2003/0104428 A1 | 6/2003 | Branton et al. |
| 2005/0053961 A1 | 3/2005 | Akeson et al. |

FOREIGN PATENT DOCUMENTS

| | | |
|---|---|---|
| GB | 2 232 769 A | 12/1990 |
| WO | WO 94/25862 A1 | 11/1994 |
| WO | WO 98/35012 A2 | 8/1998 |
| WO | WO 00/09757 A1 | 2/2000 |

(Continued)

OTHER PUBLICATIONS

Howorka et al., Sequence-specific detection of individual DNA strands using engineered nanopores. Nature Biotechnology 19:636-639 (Jul. 2001).*

(Continued)

Primary Examiner—Ethan Whisenant
(74) Attorney, Agent, or Firm—Clark & Elbing LLP; Kristina Bieker-Brady

(57) ABSTRACT

Systems and methods for analysis of polymers, e.g., polynucleotides, are provided. The systems are capable of analyzing a polymer at a specified rate. One such analysis system includes a structure having a nanopore aperture and a molecular motor, e.g., a polymerase, adjacent the nanopore aperture.

5 Claims, 14 Drawing Sheets

FOREIGN PATENT DOCUMENTS

| WO | WO 00/56937 A2 | 9/2000 |
|---|---|---|
| WO | WO 00/78668 A1 | 12/2000 |
| WO | WO 00/79257 A1 | 12/2000 |
| WO | WO 01/18251 A1 | 3/2001 |
| WO | WO 01/42782 A1 | 6/2001 |
| WO | WO 01/59684 A2 | 8/2001 |
| WO | WO 02/42496 A2 | 5/2002 |
| WO | WO 03/000920 A2 | 1/2003 |
| WO | WO 03/003446 A2 | 1/2003 |
| WO | WO 2004/077503 | 9/2004 |

OTHER PUBLICATIONS

Movileanu et al., Detecting protein that modulate teansmembrane movement of a polymer chain within a single protein pore. Nature Biotechnology 18 :1091-1095 (Oct. 2000).*

Auld et al., "A Neutral Amino Acid Change in Segment IIS4 Dramatically Alters the Gating Properties of the Voltage-Dependent Sodium Channel," *Proc. Natl. Acad. Sci. USA* 87:323-327 (1990).

Bensimon et al., "Alignment and Sensitive Detection of DNA by a Moving Interface," *Science* 265:2096-2098 (1994).

Benz et al., "Mechanism of Sugar Transport through the Sugar-Specific LamB Channel of *Escherichia coli* Outer Membrane," *J. Membr. Biol.* 100:21-29 (1987).

Benz et al., "Pore Formation by LamB of *Escherichia coli* in Lipid Bilayer Membranes," *J. Bacteriol.* 165:978-986 (1986).

Bezrukov et al., "Counting Polymers Moving through a Single Ion Channel," *Nature* 370:279-281 (1994).

Boulain et al., "Mutagenesis by Random Linker Insertion into the LamB Gene of *Escherichia coli* K12," *Mol. Gen. Genet.* 205:339-348 (1986).

Boulanger et al., "Characterization of Ion Channels Involved in the Penetration of Phage T4 DNA into *Escherichia coli* Cells," *J. Biol. Chem.* 263:9767-9775 (1988).

Boulanger et al., "Ion Channels are Likely to be Involved in the Two Steps of Phage T5 DNA Penetration into *Escherichia coli* Cells," *J. Biol. Chem.* 267:3168-3172 (1992).

Boyd et al., "Determinants of Membrane Protein Topology," *Proc. Natl. Acad. Sci. USA* 84:8525-8529 (1987).

Branton et al., "Biochemical Sensors. Adapting to Nanoscale Events," *Nature* 398:660-661 (1999).

Charbit et al., "Permissive Sites and Topology of an Outer Membrane Protein with a Reporter Epitope," *J. Bacteriol.* 173:262-275 (1991).

Dargent et al., "Effect of Point Mutations on the In-Vitro Pore Properties of Maltoporin, a Protein of *Escherichia coli* Outer Membrane," *J. Mol. Biol.* 201:497-506 (1988).

Dargent et al., "Selectivity for Maltose and Maltodextrins of Maltoporin, a Pore-Forming Protein of *E. coli* Outer Membrane," *FEBS Lett.* 220:136-142 (1987).

Deamer et al., "Characterization of Nucleic Acids by Nanopore Analysis," *Acc. Chem. Res.* 35:817-825 (2002).

DeBlois et al., "Electrokinetic Measurements with Submicron Particles and Pores by the Resistive Pulse Technique," *J. Colloid Interface Sci.* 61:323-335 (1977).

Ehrmann et al., "Genetic Analysis of Membrane Protein Topology by a Sandwich Gene Fusion Approach," *Proc. Natl. Acad. Sci. USA* 87:7574-7578 (1990).

Ferenci et al., "Channel Architecture in Maltoporin: Dominance Studies with LamB Mutations Influencing Maltodextrin Binding Provide Evidence for Independent Selectivity Filters in Each Subunit," *J. Bacteriol.* 171:855-861 (1989).

Ghadiri et al., "Artificial Transmembrane Ion Channels from Self-Assembling Peptide Nanotubes," *Nature* 369:301-304 (1994).

Hall et al., "Alamethicin. A Rich Model for Channel Behavior," *Biophys. J.* 45:233-247 (1984).

Hamill et al., "Improved Patch-Clamp Techniques for High-Resolution Current Recording from Cells and Cell-Free Membrane Patches," *Pflügers Arch.* 391:85-100 (1981).

Harrington et al., "The F Pilus of *Escherichia coli* Appears to Support Stable DNA Transfer in the Absence of Wall-to-Wall Contact between Cells," *J. Bacteriol.* 172:7263-7264 (1990).

Heinemann et al., "Open Channel Noise: IV. Estimation of Rapid Kinetics of Formamide Block in Gramicidin A Channels," *Biophys. J.* 54:757-764 (1988).

Heinemann et al., "Open Channel Noise: V. Fluctuating Barriers to Ion Entry in Gramicidin A Channels," *Biophys. J.* 57:499-514 (1990).

Henry et al., "Blockade of a Mitochondrial Cationic Channel by an Addressing Peptide: An Electrophysiological Study," *J. Membr. Biol.* 112:139-147 (1989).

Hoshi et al., "Biophysical and Molecular Mechanisms of Shaker Potassium Channel Inactivation," *Science* 250:533-538 (1990).

Hoshi et al., "Two Types of Inactivation in Shaker $K^+$ Channels: Effects of Alterations in the Carboxy-Terminal Region," *Neuron* 7:547-556 (1991).

Kasianowicz et al., "Characterization of Individual Polynucleotide Molecules Using a Membrane Channel," *Proc. Natl. Acad. Sci. USA* 93:13770-13773 (1996).

Kubitschek, "Electronic Counting and Sizing of Bacteria," *Nature* 182:234-235 (1958).

Lakey et al., "The Voltage-Dependent Activity of *Escherichia coli* Porins in Different Planar Bilayer Reconstitutions," *Eur. J. Biochem.* 186:303-308 (1989).

Lopez et al., "Hydrophobic Substitution Mutations in the S4 Sequence Alter Voltage-Dependent Gating in Shaker $K^+$ Channels," *Neuron* 7:327-336 (1991).

Li et al., "DNA Molecules and Configurations in a Solid-State Nanopore Microscope," *Nat. Mater.* 2:611-615 (2003).

Li et al., "Ion-Beam Sculpting at Nanometre Length Scales," *Nature* 412:166-169 (2001).

Meller et al., "Rapid Nanopore Discrimination between Single Polynucleotide Molecules," *Proc. Natl. Acad. Sci. USA* 97:1079-1084 (2000).

Meller and Branton, "Single Molecule Measurements of DNA Transport through a Nanopore," *Electrophoresis* 23:2583-2591 (2002).

Meller et al., "Voltage-Driven DNA Translocations through a Nanopore," *Phys. Rev. Lett.* 86:3435-3438 (2001).

Moellerfeld et al., "Improved Stability of Black Lipid Membranes by Coating with Polysaccharide Derivatives Bearing Hydrophoric Anchor Groups," *Biochem. Biophyc. Acta.* 857:265-270 (1986).

Nath et al., "Transcription by T7 RNA Polymerase Using Benzo[a]pyrene-Modified Templates," *Carcinogenesis* 12:973-976 (1991).

Neher et al., "Single-Channel Currents Recorded from Membrane of Denervated Frog Muscle Fibers," *Nature* 260:788-802 (1976).

Novick et al., "Fluorescence Measurement of the Kinetics of DNA Injection by Bacteriophage λ into Liposomes," *Biochemistry* 27:7919-7924 (1988).

Ollis et al., "Domain of *E. coli* DNA Polymerase I Showing Sequence Homology to T7 DNA Polymerase," *Nature* 313:818-819 (1985).

Ollis et al., "Structure of Large Fragment of *Escherichia coli* DNA Polymerase I Complexed with dTMP," *Nature* 313:762-766 (1985).

Ovchinnikov et al., "3. The Cyclic Peptides: Structure, Conformation, and Function: P. Gramicidin S. (851) Its Analogs and Tyrocidines A-C (904-906)," The Proteins, Third Edition 5:547-555 (1982).

Ovchinnikov et al., "3. The Cyclic Peptides: Structure, Conformation, and Function: T. Valinomycin (913)," The Proteins, Third Edition 5:563-573 (1982).

Patton et al., "Amino Acid Residues Required for Fast $Na^+$-Channel Inactivation: Charge Neutralizations and Deletions in the III-IV Linker," *Proc. Natl. Acad. Sci. USA* 89:10905-10909 (1992).

Sauer-Budge et al., "Unzipping Kinetics of Double-Stranded DNA in a Nanopore," *Phys. Rev. Lett.* 90:238101 (2003).

Shiver et al., "On the Explanation of the Acidic pH Requirement for In Vitro Activity of Colicin E1. Site-Directed Mutagenesis at Glu-468," *J. Biol. Chem.* 262:14273-14281 (1987).

Sigworth et al., "Open Channel Noise. III. High-Resolution Recordings Show Rapid Current Fluctuations in Gramicidin A and Four Chemical Analogues," *Biophys. J.* 52:1055-1064 (1987).

Simon et al., "A Protein-Conducting Channel in the Endoplasmic Reticulum," *Cell* 65:371-380 (1991).

Taylor et al., "'Reversed' Alamethicin Conductance in Lipid Bilayers," *Biophys. J.* 59:873-879 (1991).

Vercoutere et al., "Rapid Discrimination among individual DNA Hairpin Molecules at Single-Nucleotide Resolution Using an Ion Channel," *Nat. Biotechnol.* 19:248-252 (2001).

Wang et al., "Nanopores with a Spark for Single-Molecule Detection," *Nat. Biotechnol.* 19:622-623 (2001).

Weiss et al., "Molecular Architecture and Electrostatic Properties of a Bacterial Porin," *Science* 254:1627-1630 (1991).

West et al., "A Cluster of Hydrophobic Amino Acid Residues Required for Fast $Na^+$-Channel Inactivation," *Proc. Natl. Acad. Sci. USA* 89:10910-10914 (1992).

Wonderlin et al., "Optimizing Planar Lipid Bilayer Single-Channel Recordings for High Resolution with Rapid Voltage Steps," *Biophys. J.* 58:289-297 (1990).

* cited by examiner

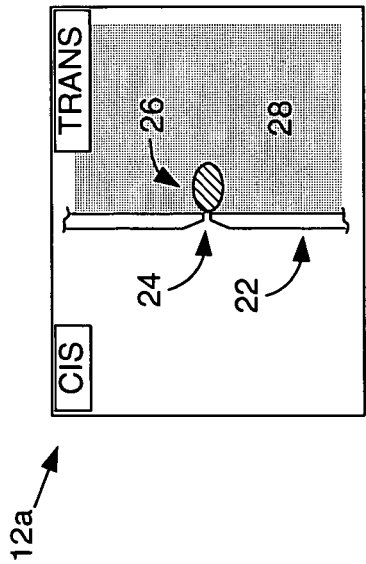
FIG. 2A
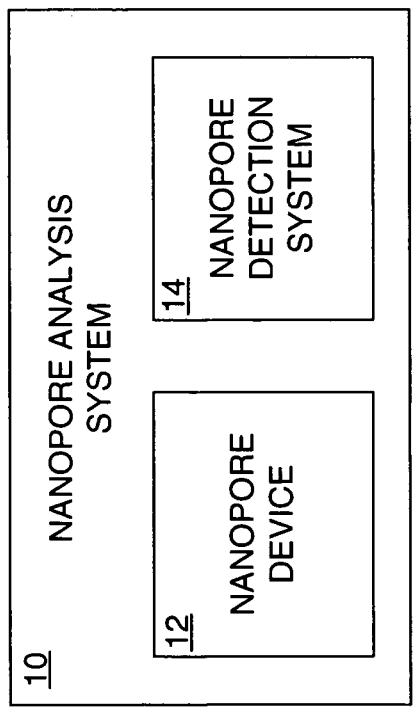
FIG. 1
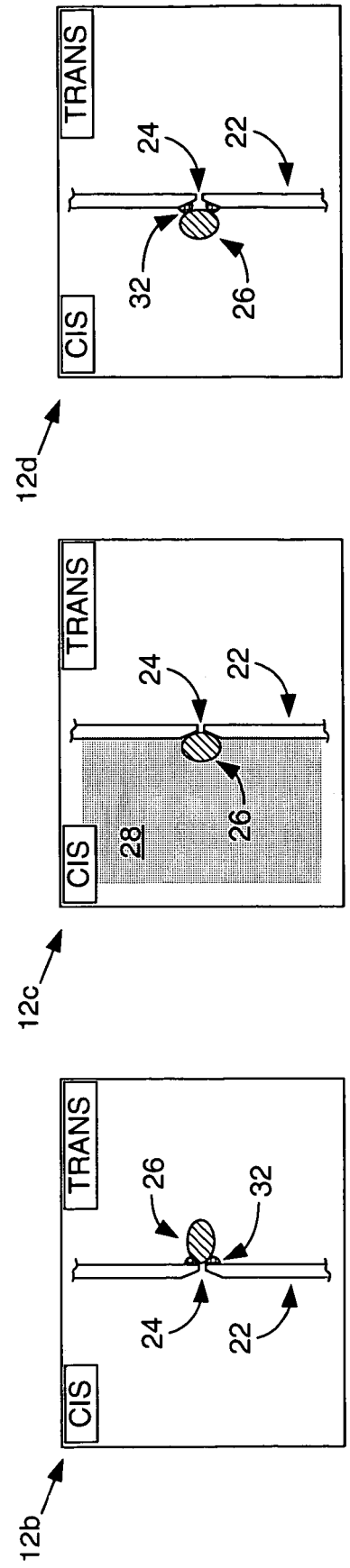
FIG. 2D
FIG. 2C
FIG. 2B

US 7,238,485 B2

METHODS AND APPARATUS FOR CHARACTERIZING POLYNUCLEOTIDES

CROSS-REFERENCE TO RELATED APPLICATIONS

This application claims benefit of U.S. Provisional Application No. 60/555,665, filed Mar. 23, 2004, hereby incorporated by reference.

STATEMENT AS TO FEDERALLY FUNDED RESEARCH

The invention was made with U.S. Government support from DARPA award number N65236-98-1-5407; DARPA/Air Force Office of Scientific Research award number F49620-01-1-0467; and NIH award numbers R01HG02338 and R01 HG01826-04. The Government has certain rights in the invention.

BACKGROUND OF THE INVENTION

The invention relates to the field of methods and apparatus for characterizing nucleic acids and other polymers.

Determining the nucleotide sequence of DNA and RNA in a rapid manner is a major goal of researchers in biotechnology, especially for projects seeking to obtain the sequence of entire genomes of organisms. In addition, rapidly determining the sequence of a nucleic acid molecule is important for identifying genetic mutations and polymorphisms in individuals and populations of individuals.

Nanopore sequencing is one method of rapidly determining the sequence of nucleic acid molecules. Nanopore sequencing is based on the property of physically sensing the individual nucleotides (or physical changes in the environment of the nucleotides (i.e., electric current)) within an individual polynucleotide (e.g., DNA and RNA) as it traverses through a nanopore aperture. In principle, the sequence of a polynucleotide can be determined from a single molecule. However, in practice, it is preferred that a polynucleotide sequence be determined from a statistical average of data obtained from multiple passages of the same molecule or the passage of multiple molecules having the same polynucleotide sequence. The use of membrane channels to characterize polynucleotides as the molecules pass through the small ion channels has been studied by Kasianowicz et al. (Proc. Natl. Acad. Sci. USA. 93:13770–3, 1996, incorporate herein by reference) by using an electric field to force single stranded RNA and DNA molecules through a 2.6 nanometer diameter nanopore aperture (i.e., ion channel) in a lipid bilayer membrane. The diameter of the nanopore aperture permitted only a single strand of a polynucleotide to traverse the nanopore aperture at any given time. As the polynucleotide traversed the nanopore aperture, the polynucleotide partially blocked the nanopore aperture, resulting in a transient decrease of ionic current. Since the length of the decrease in current is directly proportional to the length of the polynucleotide, Kasianowicz et al. were able to determine experimentally lengths of polynucleotides by measuring changes in the ionic current.

Baldarelli et al. (U.S. Pat. No. 6,015,714) and Church et al. (U.S. Pat. No. 5,795,782) describe the use of nanopores to characterize polynucleotides including DNA and RNA molecules on a monomer by monomer basis. In particular, Baldarelli et al. characterized and sequenced the polynucleotides by passing a polynucleotide through the nanopore aperture. The nanopore aperture is imbedded in a structure or an interface, which separates two media. As the polynucleotide passes through the nanopore aperture, the polynucleotide alters an ionic current by blocking the nanopore aperture. As the individual nucleotides pass through the nanopore aperture, each base/nucleotide alters the ionic current in a manner that allows the identification of the nucleotide transiently blocking the nanopore aperture, thereby allowing one to characterize the nucleotide composition of the polynucleotide and perhaps determine the nucleotide sequence of the polynucleotide.

One disadvantage of previous nanopore analysis techniques is controlling the rate at which the target polynucleotide is analyzed. As described by Kasianowicz, et al. (Proc. Natl. Acad. Sci., USA, 93:13770–3, (1996)), nanopore analysis is a useful method for performing length determinations of polynucleotides. However, the translocation rate is nucleotide composition dependent and can range between $10^5$ to $10^7$ nucleotides per second under the measurement conditions outlined by Kasianowicz et al. Therefore, the correlation between any given polynucleotide's length and its translocation time is not straightforward. It is also anticipated that a higher degree of resolution with regard to both the composition and spatial relationship between nucleotide units within a polynucleotide can be obtained if the translocation rate is substantially reduced.

SUMMARY OF THE INVENTION

The invention features apparatus for characterizing a polynucleotide, e.g., at a specified rate, and methods of its use and manufacture. Typically, an apparatus includes a nanopore aperture and a molecular motor that is capable of moving a target polynucleotide with respect to the nanopore, e.g., at a specified rate.

In one aspect, the invention features a method for analyzing a target polynucleotide including introducing the target polynucleotide to a nanopore analysis system including a nanopore aperture; allowing the target polynucleotide to move with respect to the nanopore aperture to produce a signal at a rate of 75–2000 Hz, e.g., 350–2000 Hz; and monitoring the signal corresponding to the movement of the target polynucleotide with respect to the nanopore aperture, e.g., to measure a monomer-dependent characteristic of the target polynucleotide. Examples of monomer-dependent characteristics include the identity of a nucleotide or the number of nucleotides in the polynucleotide. The nanopore analysis system may further include a molecular motor that moves the polynucleotide with respect to the nanopore aperture. The molecular motor may also be substantially immobilized inline with the nanopore aperture, e.g., by a gel matrix. The target polynucleotide may or may not move through the nanopore aperture. The method may also include applying a voltage gradient to the nanopore analysis system to draw the target polynucleotide adjacent the nanopore aperture. In another embodiment, the method includes altering the rate of movement of the polynucleotide before, during, or after the monitoring step. The movement may be increased, decreased, initiated, or stopped, e.g., at least in part, from a change in voltage, pH, temperature, viscosity, or concentration of a chemical species (e.g., ions, cofactors, energy sources, or inhibitors). In certain embodiments, the molecular motor is a DNA polymerase, an exonuclease, or a helicase, and the rate of movement is 75–2000 Hz.

In another aspect, the invention features an alternative method for analyzing a target polynucleotide including introducing the target polynucleotide to a nanopore analysis system including a nanopore aperture and a molecular motor disposed adjacent the nanopore aperture; allowing the target polynucleotide to move with respect to the nanopore aperture to produce a signal; and monitoring the signal corresponding to the movement of the target polynucleotide with respect to the nanopore aperture, e.g., to measure a monomer-dependent characteristic of the target polynucleotide. This alternative method further includes altering the rate of movement of the polynucleotide before, during, or after the monitoring. Exemplary schemes for altering the rate are described herein.

The invention further features a nanopore analysis system including a structure having a nanopore aperture; and a molecular motor adjacent the nanopore aperture, wherein the molecular motor is substantially immobilized inline with the nanopore aperture, and the molecular motor is capable of moving a polynucleotide with respect to the nanopore aperture a rate of 75–2000 Hz, e.g., at least 350 Hz. The rate of movement is controllable, e.g., by voltage, pH, temperature, viscosity, or concentration of a chemical species. The molecular motor may be substantially immobilized inline with the nanopore aperture by a gel matrix, e.g., through a covalent bond. The molecular motor may be immobilized on the cis or trans side of the structure. The system may also include a detection system operative to detect a monomer-dependent characteristic of a polynucleotide. In certain embodiments, the molecular motor is a DNA polymerase, an exonuclease, or a helicase, and the rate of movement is 75–2000 Hz.

In another aspect, the invention features a method for fabricating a nanopore analysis device including providing a structure comprising a nanopore aperture, a molecular motor, and a positioning polynucleotide; forming a complex between the positioning polynucleotide and molecular motor; disposing the complex adjacent the nanopore aperture; and immobilizing the molecular motor adjacent the nanopore aperture such that the molecular motor is substantially inline with the nanopore aperture; and removing the positioning polynucleotide from the complex. The disposing step may include applying a voltage gradient to the nanopore analysis system to draw the complex to the nanopore aperture. The immobilizing step may include disposing a gel matrix around the complex, such that the molecular motor is substantially immobilized inline with the nanopore aperture by the gel matrix. In an alternative embodiment, the immobilizing step may include reacting a chemical bonding material disposed on the structure with the molecular motor such that the molecular motor is immobilized substantially inline with the nanopore aperture by the chemical bonding material.

In various embodiments of any of the above aspects, the molecular motor includes a DNA polymerase, a RNA polymerase, a ribosome, an exonuclease, or a helicase. Exemplary DNA polymerases include *E. coli* DNA polymerase I, *E. coli* DNA polymerase I Large Fragment (Klenow fragment), phage T7 DNA polymerase, Phi-29 DNA polymerase, *Thermus aquaticus* (Taq) DNA polymerase, *Thermus flavus* (Tfl) DNA polymerase, *Thermus Thermophilus* (Tth) DNA polymerase, *Thermococcus litoralis* (Tli) DNA polymerase, *Pyrococcus furiosus* (Pfu) DNA polymerase, Vent™ DNA polymerase, *Bacillus stearothermophilus* (Bst) DNA polymerase, AMV reverse transcriptase, MMLV reverse transcriptase, and HIV-1 reverse transcriptase. Exemplary RNA polymerases include T7 RNA polymerase, T3 RNA polymerase, SP6 RNA polymerase, and *E. coli* RNA polymerase. Exemplary exonucleases include exonuclease Lambda, T7 Exonuclease, Exo III, RecJ$_1$ Exonuclease, Exo I, and Exo T. Exemplary helicases include *E-coli* bacteriophage T7 gp4 and T4 gp41 gene proteins, *E. coli* protein DnaB, *E. coli* protein RuvB, and *E. coli* protein rho. In certain embodiments, the molecular motor includes a DNA polymerase, a ribosome, an exonuclease, or a helicase, e.g., exhibiting a rate of movement of a polynucleotide of 75–2000 Hz.

By "cis" is meant the side of a nanopore aperture through which a polymer enters the pore or across the face of which the polymer moves.

By "trans" is meant the side of a nanopore aperture through which a polymer (or fragments thereof) exits the pore or across the face of which the polymer does not move.

By "molecular motor" is meant a molecule (e.g., an enzyme) that physically interacts with a polymer, e.g., a polynucleotide, and is capable of physically moving the polymer with respect to a fixed location. Although not intending to be bound by theory, molecular motors utilize chemical energy to generate mechanical force. The molecular motor may interact with each monomer of a polymer in a sequential manner.

By "polynucleotide" is meant DNA or RNA, including any naturally occurring, synthetic, or modified nucleotide. Nucleotides include, but are not limited to, ATP, dATP, CTP, dCTP, GTP, dGTP, UTP, TTP, dUTP, 5-methyl-CTP, 5-methyl-dCTP, ITP, dITP, 2-amino-adenosine-TP, 2-amino-deoxyadenosine-TP, 2-thiothymidine triphosphate, pyrrolo-pyrimidine triphosphate, 2-thiocytidine as well as the alphathiotriphosphates for all of the above, and 2'-O-methyl-ribonucleotide triphosphates for all the above bases. Modified bases include, but are not limited to, 5-Br-UTP, 5-Br-dUTP, 5-F-UTP, 5-F-dUTP, 5-propynyl dCTP, and 5-propynyl-dUTP.

By "transport property" is meant a property measurable during polymer movement with respect to a nanopore. The transport property may be, for example, a function of the solvent, the polymer, a label on the polymer, other solutes (e.g., ions), or an interaction between the nanopore and the solvent or polymer.

One advantage of using molecule motors in the apparatus and methods described herein is that they provide a mechanism for controlling the rate (e.g., from 0 to 2000 nucleotides per second) of movement of the polynucleotide of interest with respect to a nanopore aperture. Another advantage of using molecular motors is that they can selectively interact and act upon either single or double stranded polynucleotides. A further advantage of using molecular motors is that some molecular motors decrease the probability of backward movement of the polynucleotide through the nanopore aperture, thus ensuring a defined directional analysis of a polynucleotide sequence.

Other features and advantages of the invention will be apparent from the following drawings, detailed description, and the claims.

BRIEF DESCRIPTION OF THE DRAWINGS

FIG. 1 is a schematic of an embodiment of a nanopore analysis system.

FIGS. 2A through 2D are diagrams of representative nanopore devices that can be used in the nanopore analysis system of FIG. 1.

DETAILED DESCRIPTION OF THE INVENTION

Figure 3:
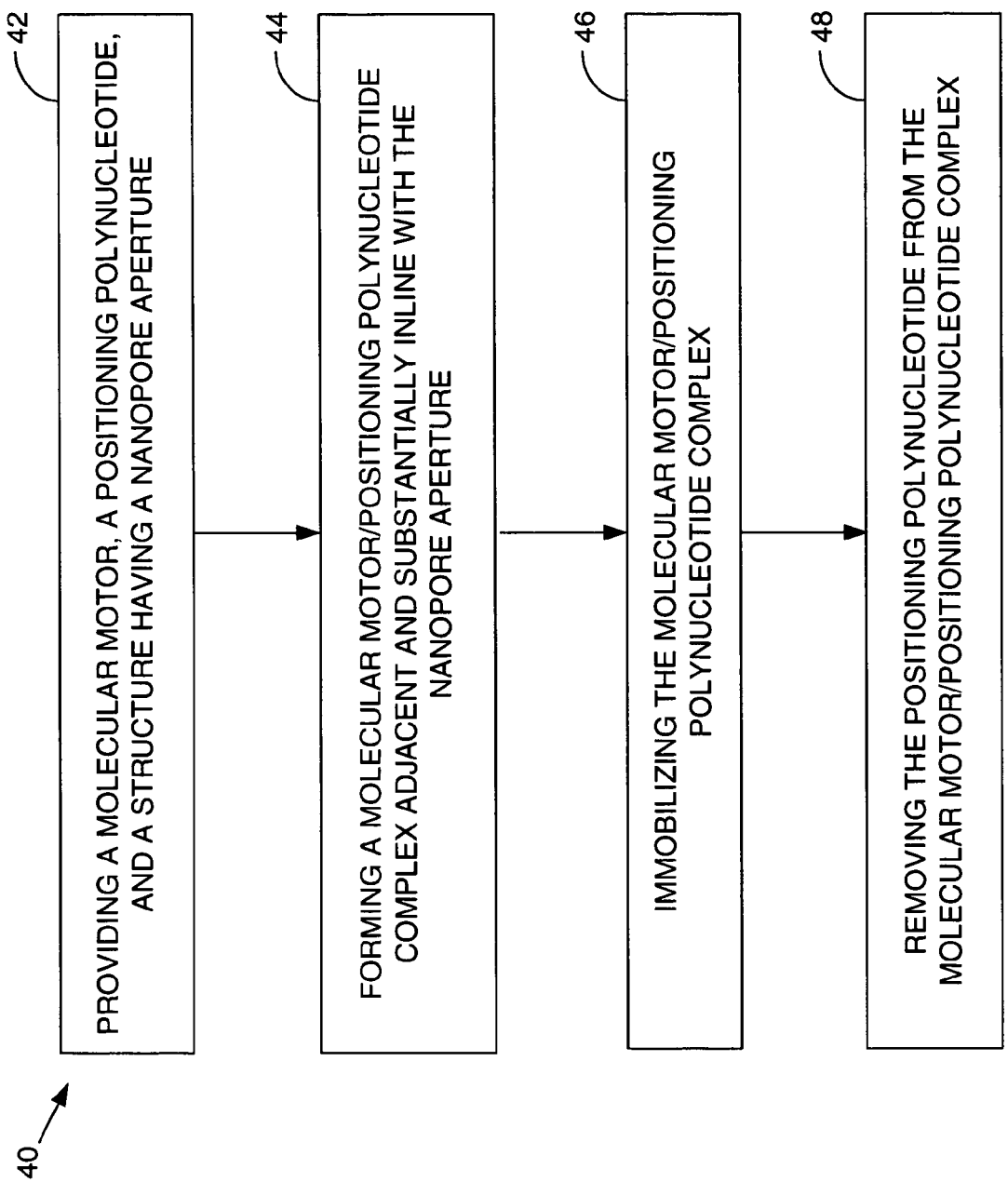
FIG. 3 is a flow diagram of a representative process for fabricating a nanopore device.

The invention features an apparatus for characterizing polymers, such as polynucleotides, e.g., at a specified rate. Typically, an apparatus of the invention includes a nanopore aperture and a molecular motor disposed adjacent the aperture, where the molecular motor is capable of moving a polymer with respect to the aperture. In alternative embodiments, other methods are employed to control the rate of movement of the polymer. By making measurements as the polymer is moved, the polymer may be characterized. The following discussion will focus on polynucleotides, but the invention is applicable to any other polymer (e.g., proteins, polypeptides, polysaccharides, lipids, and synthetic polymers) that can be moved via a molecular motor.

Apparatus

FIG. 1 illustrates a representative embodiment of a nanopore analysis system 10 that can be used in characterizing polymers such as polynucleotides. The nanopore analysis system 10 includes, but is not limited to, a nanopore device 12 and a nanopore detection system 14. The nanopore device 12 and the nanopore detection system 14 are coupled so that data regarding the target polynucleotide can be measured.

A typical nanopore detection system 14 includes electronic equipment capable of measuring characteristics of the polynucleotide as it interacts with the nanopore aperture, a computer system capable of controlling the measurement of the characteristics and storing the corresponding data, control equipment capable of controlling the conditions of the nanopore device, and one or more detectors capable of measuring transport properties in the device.

The nanopore detection system 14 can measure transport properties, such as, but not limited to, the amplitude or duration of individual conductance or electron tunneling current changes across a nanopore aperture. Such changes can identify the monomers in sequence, as each monomer has a characteristic conductance change signature. For instance, the volume, shape, or charges on each monomer can affect conductance in a characteristic way. Likewise, the size of the entire polynucleotide can be determined by observing the length of time (duration) that monomer-dependent conductance changes occur. Alternatively, the number of nucleotides in a polynucleotide (also a measure of size) can be determined as a function of the number of nucleotide-dependent conductance changes for a given nucleic acid traversing the nanopore aperture. The number of nucleotides may not correspond exactly to the number of conductance changes, because there may be more than one conductance level change as each nucleotide of the nucleic acid passes sequentially through the nanopore aperture. However, there is a proportional relationship between the two values that can be determined by preparing a standard with a polynucleotide having a known sequence. Other detection schemes are described herein.

FIGS. 2A through 2D illustrate representative embodiments of a nanopore device 12a . . . 12d. The nanopore device 12a . . . 12d includes, but is not limited to, a structure 22 that separates two independent adjacent pools of a medium. The two adjacent pools are located on the cis side and the trans side of the nanopore device 12a . . . 12d. The structure 22 includes, but is not limited to, at least one nanopore aperture 24, e.g., so dimensioned as to allow sequential monomer-by-monomer translocation (i.e., passage) from one pool to another of only one polynucleotide at a time, and detection components that can be used to measure transport properties.

Exemplary detection components have been described in WO 00/79257 and can include, but are not limited to, electrodes directly associated with the structure 22 at or near the pore aperture, and electrodes placed within the cis and trans pools. The electrodes may be capable of, but limited to, detecting ionic current differences across the two pools or electron tunneling currents across the pore aperture.

Nanopores. The structure 22 contains one or more nanopore apertures 24 and may be made of any appropriate material, such as, but not limited to, silicon nitride, silicon oxide, mica, polyimide, or lipids. The structure 22 may further include detection electrodes and detection integrated circuitry. The nanopore aperture 24 may be a simple aperture in structure 22 or it may be composed of other materials, such as proteins, that can assemble so as to produce a channel through structure 22. The nanopore aperture may be dimensioned so that only a single stranded polynucleotide can pass through the nanopore aperture 24 at a given time, so that a double or single stranded polynucleotide can pass through the nanopore aperture 24, so that neither a single nor a double stranded polynucleotide can pass through the nanopore aperture 24, or so that more than one double stranded polynucleotide can pass through the nanopore aperture 24. A molecular motor 26 disposed adjacent to a nanopore aperture 24 can be used to determine whether a single or double stranded polynucleotide is analyzed by the nanopore analysis system 10 and the type of polynucleotide (e.g., RNA or DNA and single or double stranded) that may pass through the nanopore aperture 24. The nanopore aperture 24 may have a diameter of, e.g., 3 to 20 nanometers (for analysis of single or double stranded polynucleotides), and of, e.g., 1.6 to 4 nanometers (for analysis of single stranded polynucleotides). When a molecular motor is employed, the size of the nanopore aperture 24 may be significantly larger than the radial dimension of a polynucleotide.

Any nanopore of the appropriate size may be used in the methods of the invention. Nanopores may be biological, e.g., proteinaceous, or solid-state. Suitable nanopores are described, for example, in U.S. Pat. Nos. 6,746,594, 6,673,615, 6,627,067, 6,464,842, 6,362,002, 6,267,872, 6,015,714, and 5,795,782 and U.S. Publication Nos. 2004/0121525, 2003/0104428, and 2003/0104428. An exemplary method for fabricating solid-state membranes is the ion beam sculpting method described in Li et al. Nature 412:166 (2001) and in Chen et al. Nano Letters 4:1333 (2004).

Molecular Motors.

Any molecular motor that is capable of moving a polynucleotide of interest may be employed in the apparatus of the invention. Desirable properties of a molecular motor include: sequential action, e.g., addition or removal of one nucleotide per turnover; no backtracking along the target polynucleotide; no slippage of the motor on the target polynucleotide due to forces, e.g., from an electric field, employed to drive a polynucleotide to the motor; retention of catalytic function when disposed adjacent a nanopore aperture; high processivity, e.g., the ability to remain bound to target polynucleotide and perform at least 1,000 rounds of catalysis before dissociating.

A molecular motor 26 includes, e.g., polymerases (i.e., DNA and RNA), helicases, ribosomes, and exonucleases. The molecular motor 26 that is used according to the methods described herein will depend, in part, on the type of target polynucleotide being analyzed. For example, a molecular motor 26 such as a DNA polymerase or a helicase is useful when the target polynucleotide is DNA, and a molecular motor such as RNA polymerase is useful when the target polynucleotide is RNA. In addition, the molecular motor 26 used will depend, in part, on whether the target polynucleotide is single-stranded or double-stranded. Those of ordinary skill in the art would be able to identify the appropriate molecular motors 26 useful according to the particular application.

DNA polymerases have been demonstrated to function as efficient molecular motors 26. Exemplary DNA polymerases include *E. coli* DNA polymerase I, *E. coli* DNA polymerase I Large Fragment (Klenow fragment), phage T7 DNA polymerase, Phi-29 DNA polymerase, thermophilic polymerases (e.g., *Thermus aquaticus* (Taq) DNA polymerase, *Thermus flavus* (Tfl) DNA polymerase, *Thermus Thermophilus* (Tth) DNA polymerase, *Thermococcus litoralis* (Tli) DNA polymerase, *Pyrococcus furiosus* (Pfu) DNA polymerase, Vent™ DNA polymerase, or *Bacillus stearothermophilus* (Bst) DNA polymerase), and a reverse transcriptase (e.g., AMV reverse transcriptase, MMLV reverse transcriptase, or HIV-1 reverse transcriptase). Other suitable DNA polymerases are known in the art. In one embodiment, approximately 300 nucleotides per second are threaded through the clamp of a DNA polymerase in a ratchet-like linear fashion, which decreases the probability of backward movement of the polynucleotide. In certain embodiments, *E. coli* DNA polymerase I, the Klenow fragment, phage T7 DNA polymerase, Taq polymerase, and the Stoffel fragment are excluded from the molecular motors employed in the invention.

RNA polymerases, like DNA polymerases, can also function as efficient molecular motors 26. Exemplary RNA polymerases include T7 RNA polymerase, T3 RNA polymerase, SP6 RNA polymerase, and *E. coli* RNA polymerases. In certain embodiments, T7 RNA polymerase is excluded from the molecular motors employed in the invention.

The molecular motor 26 may also include a single-strand specific or double-strand specific exonuclease. Exonuclease Lambda, which is a trimeric enzyme isolated from the *E. coli* bacteriophage Lambda, is particularly well suited to be the molecular motor 26 for a number of reasons. First, it acts upon double-stranded DNA, which is a preferred substrate for genetic analysis. Second, it is a highly processive enzyme and acts upon only one strand of the double-stranded DNA, which facilitates the movement of a given DNA molecule with respect to a nanopore aperture 24. Further, the digestion rate is about 10–50 nucleotides per second (van Oijen et al. Science 301:1235 (2003); Perkins et al. Science 301:1914 (2003)). Exonuclease Lambda may also be excluded from the molecular motors employed in the invention. Additional exonucleases include, for example, T7 Exonuclease, Exo III, RecJ$_1$ Exonuclease, Exo I, and Exo T.

Another type of molecular motor 26 is a helicase. Helicases are proteins, which move along polynucleotide backbones and unwind the polynucleotide so that the processes of DNA replication, repair, recombination, transcription, mRNA splicing, translation, and ribosomal assembly, can take place. Helicases include both RNA and DNA helicases. Helicases have previously been described in U.S. Pat. No. 5,888,792. Exemplary helicases include hexameric helicases such as the *E-coli* bacteriophage T7 gp4 and T4 gp41 gene proteins, and the *E. coli* proteins DnaB, RuvB, and rho (for review see: West S C, *Cell*, 86, 177–180 (1996)). Hexameric helicases unwind double stranded DNA in a 5'-3' direction, which ensures a directional analysis of the DNA target molecules. In addition, some of the helicases have processive translocation rates in excess of 1000 nucleotides per second (Roman et al. J. Biol. Chem. 267:4207 (1992). In addition, these hexameric helicases form a ring structure having an inside hole dimension ranging in size from 2–4 nanometers and an outside ring dimension of about 14 nanometers, which is within the dimension limits of a useful molecular motor 26. The hexameric ring structure is formed and stabilized in the presence of $Mg^{+2}$ and some type of nucleotide (NMP, NDP or NTP).

A molecular motor 26 may be disposed on the cis or trans side of a nanopore device 12a . . . 12d. In either case, the molecular motor 26 can be substantially immobilized, but need not be immobilized, adjacent the nanopore aperture 26 and inline with the nanopore aperture 26 by a matrix material 28, by chemically bonding with the structure using chemical bonding materials 32, or by any other appropriate mechanism (e.g., noncovalent interactions). A molecular motor 26 may also be wholly or partially disposed within a nanopore aperture 24.

The matrix material 28 may encase the molecular motor 26 and substantially immobilizes the molecular motor 26. Desirable properties of matrix material 28 include (a) the ability to be cast, in situ, around a localized molecular motor 26 or positioning polynucleotide/molecular motor complex positioned adjacent and substantially inline with the nanopore aperture 24 without affecting the molecular motors activity, (b) the ability to sufficiently immobilize the molecular motor 26 so that it does not diffuse away from the nanopore aperture 24, and (c) the ability to permit the target polynucleotide to sufficiently migrate through the matrix material 28 to the molecular motor 26 and nanopore aperture 24. Exemplary matrix materials 28 include natural polymers (e.g., agar, agarose, and other polysaccharide-based materials), synthetic polymers, and sol-gels.

Synthetic polymers can include, but are not limited to, polyacrylamides, which can be polymerized chemically or through irradiation with UV light, X-rays or gamma rays. These types of matrices have been used to immobilize and entrap molecular motor enzymes 26 for a variety of applications. For example, penicillin acylase has been shown to maintain enzymatic activity when embedded within acrylamide polymers having varying degrees of porosity and cross-linking (Prabhune A., and Sivaraman H., *Applied Biochem. and Biotech.* 30, 265–272 (1991), Wuyun G W, et al. *Acta Chirnica Sinica,* 60 504–508 (2002)). Alkaline phosphatase has been immobilized by physical entrapment with colloidal particles having functionalized surfaces comprising copolymers of acrylamide (Daubresse et al., *Colloid and Polymer Science,* 274, 482–489 (1996) and Daubresse et al., *J. of Colloid and Interface Science,* 168, 222–229 (1994)).

The molecular motor 26 may also be covalently linked to the matrix material 28 to prevent the molecular motor 26 from diffusing away from the nanopore aperture 24. This may be particularly important when using lower density polymer matrices that enable larger substrate molecules (e.g., >1 kb polynucleotides) to freely migrate through the matrix material 28. The covalent linkage between the molecular motor 26 and matrix material 28 may be formed by any one of a number of methods known in the art. Direct linkage between natural amino acid residues such as lysine or cysteine within the molecular motor 26 and the matrix material 28 can be formed using chemical methods. The molecular motor 26 may be engineered to contain desired residues for specific linking chemistries. A synthetic linker having a defined reactive moiety (e.g., N,N'-methylenebisacrylamide) can be attached to the molecular motor 26 prior to immobilization so that the molecular motor 26 becomes linked to the matrix material 28 during the matrix material 28 formation process In another embodiment, a chemical bonding material 32 can be disposed onto the structure to chemically bond (e.g., covalent and non-covalent bonding) the molecular motor 26 to the structure 22. The chemical bonding material 32 is positioned so that the bound molecular motor 26 is adjacent and substantially inline with the nanopore aperture 24. The chemical bonding between the chemical bonding material 32 and the molecular motor 26 can include, but is not limited to, bonding between amine, carboxylate, aldehyde and sulfhydryl functional groups on the molecular motor 26 and the chemical bonding material 32 through linker or chemical conjugations involving reactive groups such isothiocyanates, acyl azides, NHS esters, sulfonyl chlorides, epoxides, carbonates, carbodiimides and anhydrides (see: G. T. Hermanson, *Bioconjugate Techniques* (1996), Academic Press, Inc., San Diego Calif.). Thus, the chemical bonding material 32 can include, but is not limited to, compositions having groups such as isothiocyanates, acyl azides, NHS esters, sulfonyl chlorides, epoxides, carbonates, carbodiimides, and anhydrides.

In another embodiment, the molecular motor 26 can be substantially immobilized adjacent and inline with the nanopore aperture 24 by using a matrix material 28 and a chemical bonding material 32.

Media. The medium disposed in the pools on either side of the substrate 22 may be any fluid that permits adequate polynucleotide mobility for substrate interaction. Typically, the medium is a liquid, usually aqueous solutions or other liquids or solutions in which the polynucleotides can be distributed. When an electrically conductive medium is used, it can be any medium, which is able to carry electrical current. Such solutions generally contain ions as the current-conducting agents (e.g., sodium, potassium, chloride, calcium, magnesium, cesium, barium, sulfate, or phosphate). Conductance across the nanopore aperture 24 can be determined by measuring the flow of current across the nanopore aperture via the conducting medium. A voltage difference can be imposed across the barrier between the pools using appropriate electronic equipment. Alternatively, an electrochemical gradient may be established by a difference in the ionic composition of the two pools of medium, either with different ions in each pool, or different concentrations of at least one of the ions in the solutions or media of the pools. Conductance changes are measured by the nanopore detection system 14 and are indicative of monomer-dependent characteristics.

Fabrication. An apparatus of the invention may be fabricated by any method known in the art. FIG. 3 is a flow diagram illustrating a representative process 40 for fabricating the nanopore device 12a . . . 12d. As shown in FIG. 3, the process may be construed as beginning at block 42, where a molecular motor 26, a positioning polynucleotide, and a structure 22 have a nanopore aperture 24 are provided. In block 44, a molecular motor/positioning polynucleotide complex is formed adjacent and substantially inline with the nanopore aperture 24. In block, 46, the molecular motor/positioning polynucleotide complex is substantially immobilized adjacent and substantially inline with the nanopore aperture 24. In block 48, the positioning polynucleotide is removed from the molecular motor/positioning polynucleotide complex, but the molecular motor 26 is substantially immobilized adjacent and substantially inline with the nanopore aperture 24.

Figure 4A:
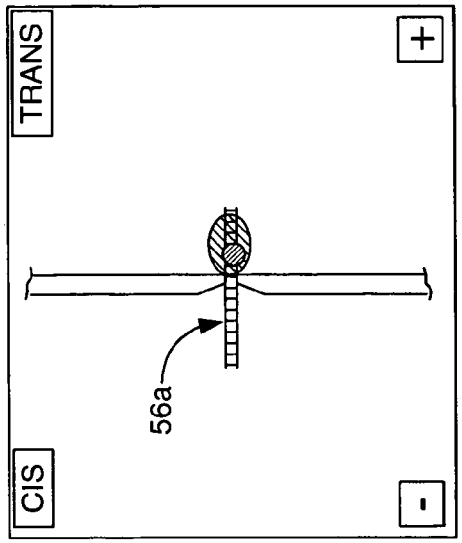
FIG. 4A through 4D are diagrams of a representative process for fabricating a representative nanopore device having a molecular motor disposed on the trans side of the nanopore device.

FIGS. 4A through 4D illustrate a representative method for fabricating a nanopore device 12a where the molecular motor 26 is immobilized by a matrix material 28 on the trans side of the nanopore device 12a. FIG. 4A illustrates the nanopore device 12a having a positioning polynucleotide 54 on the cis side of the nanopore device 12a, a structure 22 dividing the cis and trans side of the nanopore device 12a, and a molecular motor 26 and a stalling reagent 52 on the trans side of the nanopore device 12a. Not all embodiments require a stalling reagent 52 (e.g., nucleotide analogue inhibitor or non-hydrolyzable NTP analogues), and the need for a stalling reagent 52 can be determined by the type of molecular motor 26 used. For example, most molecule motors will cease to function (stall) or nearly cease to function at low temperatures approaching 0° C. Other motors, e.g., λ-exonuclease, will stall when there is no Mg$^{2+}$ in the surrounding medium. In addition, the positioning polynucleotide 54 may contain strand portions that stall the process.

Figure 4B:
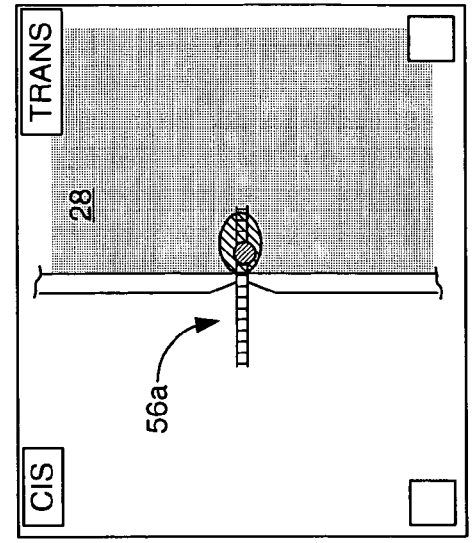

Subsequently, a voltage gradient is applied to the nanopore device 12a to draw the positioning polynucleotide 54 to the cis side of the nanopore aperture 24. In addition, the molecular motor 26 and the stalling reagent 52 are drawn to the trans side of the nanopore aperture 24. FIG. 4B illustrates the formation of the positioning polynucleotide/molecular motor complex 56a at the nanopore aperture 24, so that the complex 56a is positioned adjacent the nanopore aperture 24 and substantially inline with the nanopore aperture 24. The positioning polynucleotide 54 is partially drawn into the molecular motor 26, where the stalling reagent 52 stalls (e.g., slows down the digestion or polymerization) the translocation process of the positioning polynucleotide 54. At this point the voltage bias needed for positioning, e.g., >80 mV, may be reduced to a "holding bias," e.g., 40–80 mV, or turned off completely.

Figure 4C:
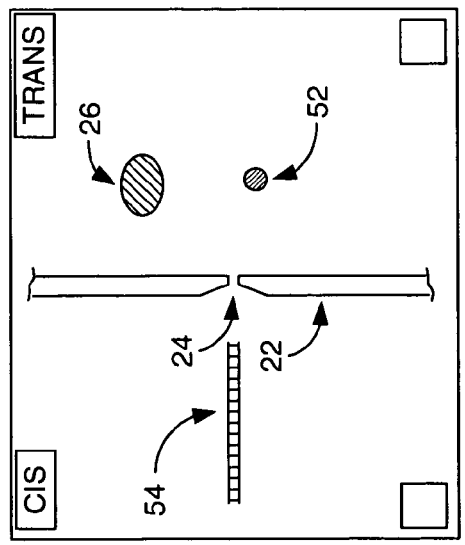
Figure 4D:
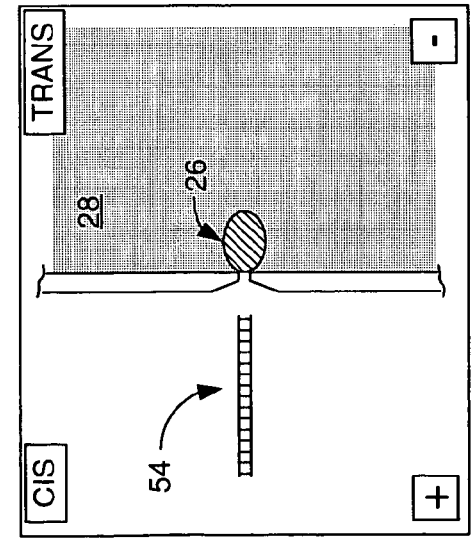

FIG. 4C illustrates the addition of matrix material 28 to the trans side of the nanopore device 12a. The matrix material 28 substantially immobilizes the positioning polynucleotide/molecular motor complex 56a adjacent the nanopore aperture 24 and substantially inline with the nanopore aperture 24. FIG. 4D illustrates the removal of the positioning polynucleotide 54 from the complex 56a by applying a voltage gradient of opposite polarity to that used to position the polynucleotide-motor complex. Alternatively, the positioning polynucleotide 54 can be removed from the complex 56a by continuing the digestion or polymerization of the positioning polynucleotide 54 after removal of the stalling reagent 52. The molecular motor 26 is substantially immobilized by the matrix material 28 adjacent the nanopore aperture 24 and substantially inline with the nanopore aperture 24. The nanopore device 12a, in which the molecular motor 26 is immobilized by adsorption to the material in which the nanopore is formed or by a matrix material 28 on the trans side, is now ready for target polynucleotide analysis.

Some types of molecular motors 26 may employ positioning polynucleotides 54 that are modified. One skilled in the art will be able to provide appropriate modified positioning polynucleotides, as required for a particular molecular motor. For example, when the molecular motor 26 is a DNA polymerase located on the trans side of the nanopore device, the positioning double-stranded polynucleotide 54 has a break, or nick, in the phosphodiester backbone towards one termini of the DNA duplex. This creates a free 3'-terminal hydroxyl to serve as an initiation site for the DNA polymerase. When a nicked strand is employed, the action of the polymerase will dislodge the strand hybridized 3' to the nick, and this dislodged strand may be the target polynucleotide. In another example, when the molecular motor 26 is a DNA polymerase located on the cis side of the nanopore device, the positioning polynucleotide 54 has either a nick or a primer that has strand-invaded and hybridized to some portion of the double-strand DNA, which can serve as a template for the DNA polymerase. In both of these cases, a stalling reagent 52 such as a nucleotide analogue inhibitor (e.g., aphidicolin) may be added to stabilize the positioning polynucleotide/molecular motor complex 56a while the complex 56a is bonded to the structure 22 or a matrix material 28 is added to the nanopore device 12a. In another example, the polymerase is a RNA polymerase, and the positioning polynucleotide 54 is coupled to a nascent RNA strand (e.g., about 10 to 100 nucleotides). After formation of the positioning polynucleotide/RNA polymerase complex, the nascent RNA strand can be drawn into the nanopore aperture 24.

In another embodiment, when the molecular motor 26 is Lambda exonuclease, the positioning polynucleotide 54 may have a recessed 5'-phosphorylated termini. Once the positioning polynucleotide 54 is drawn into the exonuclease to form the positioning polynucleotide/exonuclease complex, the positioning polynucleotide/exonuclease complex can be stalled by incorporating thiophosphate modifications into the digested positioning DNA strand.

In still another embodiment, when the molecular motor 26 is a helicase, the positioning polynucleotide 54 need not have any modifications. However, after the positioning polynucleotide/helicase complex forms, the strand separation can be stalled with the addition of non-hydrolyzable NTP analogues. Subsequently, the positioning polynucleotide 54 can be removed from the positioning polynucleotide/helicase complex by reversing the polarity of the nanopore device 12a or the positioning polynucleotide 54 can be digested with the addition ATP.

Figure 5A:
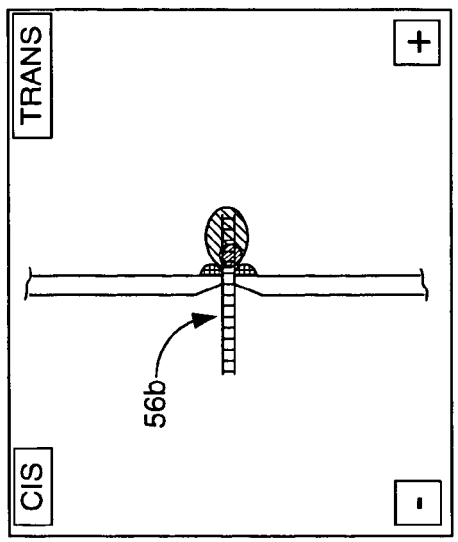
FIG. 5A through 5C are diagrams of a representative process for fabricating a representative nanopore device having a molecular motor disposed on the cis side of the nanopore device.
Figure 5B:
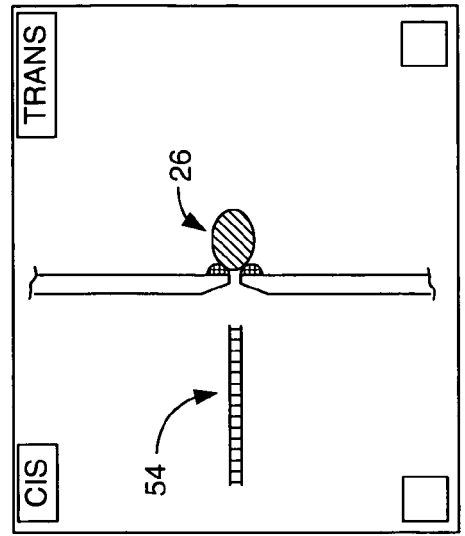
Figure 5C:
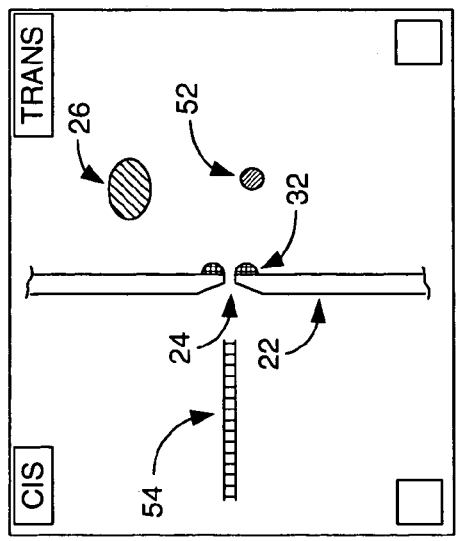

FIGS. 5A through 5C illustrate a representative method for fabricating a nanopore device 12b in which the molecular motor 26 is immobilized by bonding to the structure 22 on the trans side of the nanopore device 12b. FIG. 5A illustrates the nanopore device 12b having a positioning polynucleotide 54 on the cis side of the nanopore device 12b, a structure 22 dividing the cis and trans side of the nanopore device 12a, and a molecular motor 26 and a stalling reagent 52 on the trans side of the nanopore device 12a. In addition, the structure 22 includes chemical bonding material 32 disposed on the trans side of the structure 22 near the nanopore aperture 24. A voltage gradient is applied to the nanopore device 12a to draw the positioning polynucleotide 54 to the cis side of the nanopore aperture 24. In addition, the molecular motor 26 and the stalling reagent 52 are drawn to the trans side of the nanopore aperture 24.

FIG. 5B illustrates the formation of the positioning polynucleotide/molecular motor complex 56b at the nanopore aperture 24, so that the complex 56b is positioned adjacent the nanopore aperture 24 and substantially inline with the nanopore aperture 24. The positioning polynucleotide 54 is partially drawn into the molecular motor 26, where the stalling reagent 52 stalls the translocation process of the positioning polynucleotide 54. At this point the bias needed for positioning, e.g., >80 mV, may be reduced to a "holding bias," e.g., 40–80 mV, or turned off completely. The molecular motor 26 chemically bonds with the chemical bonding material 32 disposed on the structure 22, so that the positioning polynucleotide/molecular motor complex 56b is substantially immobilized and positioned substantially inline with the nanopore aperture 24. At this point the bias needed for positioning, e.g., >80 mV, may be reduced to a "holding bias," e.g., 40–80 mV, or turned off completely.

FIG. 5C illustrates the removal of the positioning polynucleotide 54 by applying a voltage gradient of opposite polarity to that of the positioning bias.

Alternatively, the positioning polynucleotide 54 can be removed from the complex 56a by continuing the digestion or polymerization of the positioning polynucleotide 54 after removal of the stalling reagent 52. The molecular motor 26 is substantially immobilized because it is chemically bonded to the chemical bonding material 32 adjacent the nanopore aperture 24 and substantially inline with the nanopore aperture 24. The nanopore device 12b where the molecular motor 26 is immobilized by bonding to the structure 24 on the trans side of the nanopore device 12b is now ready for target polynucleotide analysis.

Figure 6A:
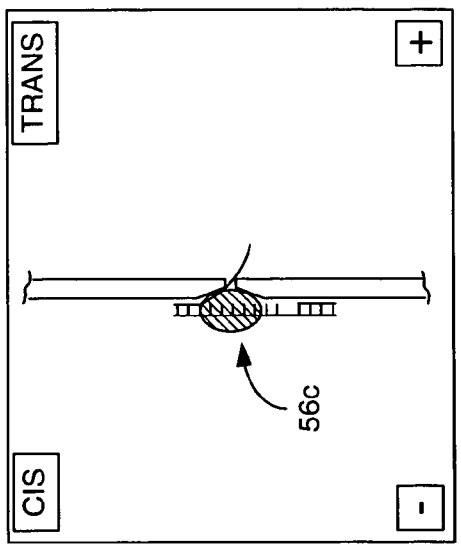
FIG. 6A through 6D are diagrams of a representative process for fabricating another representative nanopore device having a molecular motor disposed on the trans side of the nanopore device.

FIG. 6A through 6D illustrate a representative method for fabricating a nanopore device 12c, in which the molecular motor 26 is immobilized by a matrix material 28 on the cis side of the nanopore device 12c. FIG. 6A illustrates the nanopore device 12c having a positioning polynucleotide/molecular motor complex 56c disposed on the cis side of the nanopore device 12c and a structure 22 dividing the cis and trans side of the nanopore device 12c. A voltage gradient is applied to the nanopore device 12c to draw the positioning polynucleotide/molecular motor complex 56c to the cis side of the nanopore aperture 24.

Figure 6B:
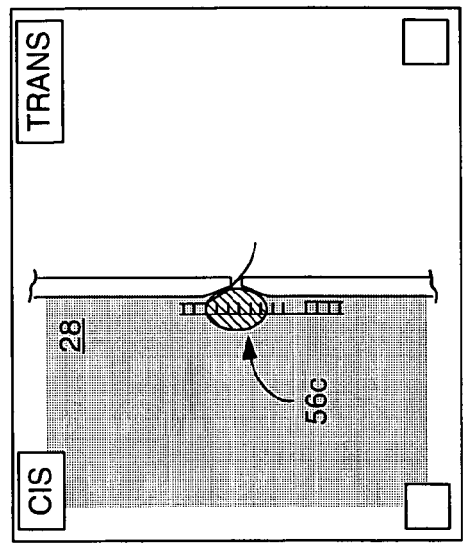

FIG. 6B illustrates the positioning of the positioning polynucleotide/molecular motor complex 56c at the nanopore aperture 24 adjacent the nanopore aperture 24 and substantially inline with the nanopore aperture 24. At this point the bias needed for positioning, e.g., >80 mV, may be reduced to a "holding bias," e.g., 40–80 mV, or turned off completely.

Figure 6C:
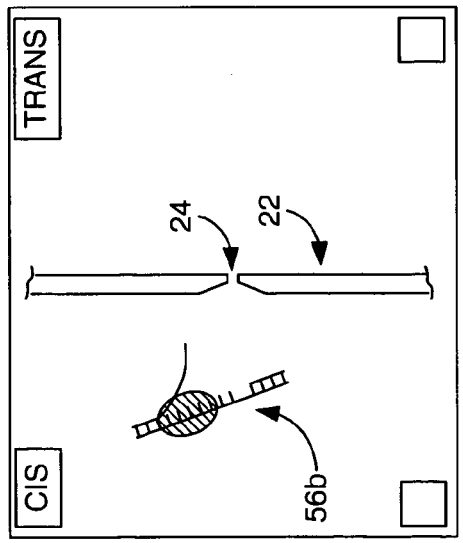
Figure 6D:
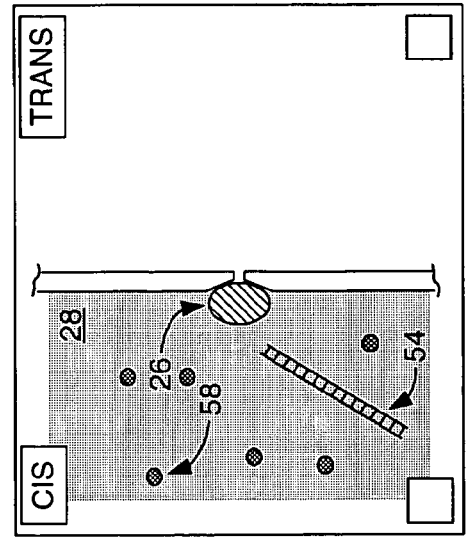

FIG. 6C illustrates the addition of the matrix material 28 to the cis side of the nanopore device 12c. The matrix material 28 substantially immobilizes the positioning polynucleotide/molecular motor complex 56c substantially inline with the nanopore aperture 24. FIG. 6D illustrates the removal of the positioning polynucleotide 54 adding nucleotide triphosphates 58. The molecular motor 26 is substantially immobilized by the matrix material 28 adjacent the nanopore aperture 24 and substantially inline with the nanopore aperture 24. The nanopore device 12c in which the molecular motor 26 is immobilized by a matrix material 28 on the cis side of the nanopore device 12c is now ready for target polynucleotide analysis.

Figure 7A:
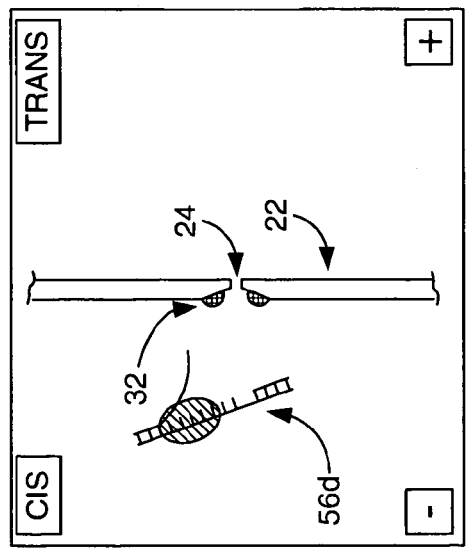
FIG. 7A through 7C are diagrams of a representative process for fabricating another representative nanopore device having a molecular motor disposed on the cis side of the nanopore device.
Figure 7B:
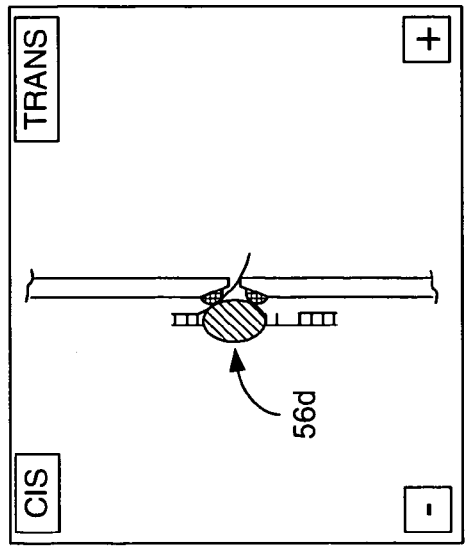
Figure 7C:
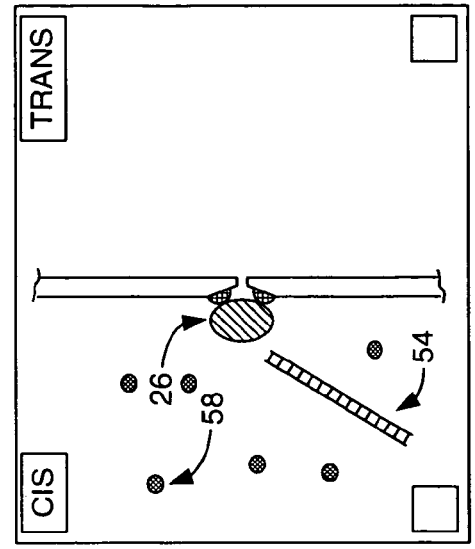

FIGS. 7A through 7C illustrate a representative method for fabricating a nanopore device 12d in which the molecular motor 26 is immobilized by bonding to the structure 22 on the cis side of the nanopore device 12d. FIG. 7A illustrates the nanopore device 12d having a positioning polynucleotide/molecular motor complex 56d disposed on the cis side of the nanopore device 12d and a structure 22 dividing the cis and trans side of the nanopore device 12d. In addition, the structure 22 includes chemical bonding material 32 disposed on the cis side of the structure 22 near the nanopore aperture 24. A voltage gradient is applied to the nanopore device 12d to draw the positioning polynucleotide/molecular motor complex 56d to the cis side of the nanopore aperture 24.

FIG. 7B illustrates the positioning of the positioning polynucleotide/molecular motor complex 56d at the nanopore aperture 24 adjacent the nanopore aperture 24 and substantially inline with the nanopore aperture 24. At this point the bias needed for positioning, e.g., >80 mV, may be reduced to a "holding bias," e.g., 40–80 mV, or turned off completely. The molecular motor 26 chemically bonds with the chemical bonding material 32 disposed on the structure 22, so that the positioning polynucleotide/molecular motor complex 56d is substantially immobilized and positioned substantially inline with the nanopore aperture 24. At this point the bias needed for positioning, e.g., >80 mV, may be reduced to a "holding bias," e.g., 40–80 mV, or turned off completely.

FIG. 7C illustrates the removal of the positioning polynucleotide 54. The molecular motor 26 is substantially immobilized because it is chemically bonded to the chemical bonding material 32 adjacent the nanopore aperture 24 and substantially inline with the nanopore aperture 24. The nanopore device 12d where the molecular motor 26 is immobilized by bonding to the structure 22 on the cis side of the nanopore device 12d is now ready for target polynucleotide analysis.

Detection. Time-dependent transport properties of the nanopore aperture may be measured by any suitable technique. The transport properties may be a function of the medium used to transport the polynucleotide, solutes (e.g., ions) in the liquid, the polynucleotide (e.g., chemical structure of the monomers), or labels on the polynucleotide. Exemplary transport properties include current, conductance, resistance, capacitance, charge, concentration, optical properties (e.g., fluorescence and Raman scattering), and chemical structure.

Desirably, the transport property is current. Suitable methods for detecting current in nanopore systems are known in the art, for example, as described in U.S. Pat. Nos. 6,746,594, 6,673,615, 6,627,067, 6,464,842, 6,362,002, 6,267,872, 6,015,714, and 5,795,782 and U.S. Publication Nos. 2004/0121525, 2003/0104428, and 2003/0104428. In another embodiment, the transport property is electron flow across the diameter of the aperture, which may be monitored by electrodes disposed adjacent to or abutting on the nanopore circumference.

Methods of Characterizing Polynucleotides

In general, nanopore characterization of polynucleotides involves the use of two separate pools of a medium and an interface between the pools. The interface between the pools is capable of interacting sequentially with the individual monomer residues of a polynucleotide present in one of the pools. Measurements of transport properties are continued over time, as individual monomer residues of the polynucleotide interact sequentially with the interface, yielding data suitable to determine a monomer-dependent characteristic of the polynucleotide. The monomer-dependent characterization achieved by nanopore sequencing may include identifying characteristics such as, but not limited to, the number and composition of monomers that make up each individual polynucleotide, in sequential order.

The target polynucleotide being characterized may remain in its original pool (not depicted), or it, or a reaction product including it or fragments thereof, may cross the nanopore aperture into the other pool (depicted in FIGS. 9 and 10). In either situation, the target polynucleotide moves in relation to the nanopore aperture, and individual nucleotides interact sequentially with the nanopore aperture, giving rise to a change in the measured transport properties, e.g., conductance, of the nanopore aperture. When the polynucleotide does not cross into the trans side of the device, it is held adjacent the nanopore aperture such that its nucleotides interact with the nanopore aperture passage and bring about the changes in transport properties, which are indicative of polynucleotide characteristics.

Absent molecular motors, single stranded DNA molecules can be driven through the α-hemolysin nanopore by a voltage bias at about 1–2 nucleotides per microsecond, and dsDNA translocates through synthetic nanopores approximately two orders of magnitude faster. Individual nucleotides may not be reliably resolved by measurement of ionic current at such high rates of transfer. In some embodiments, the methods of the invention operate by modifying the intrinsic rate of polynucleotide translocation through a pore, e.g., via use of a molecular motor. The approach is to add native DNA or RNA to the cis compartment of the nanopore sensor in association with a nucleic acid processing enzyme, e.g., an exonuclease, a helicase, or a polymerase. In one embodiment, the single-stranded product of the enzyme-nucleic acid complex is then drawn into the pore while the enzyme acts upon the nucleic acid substrate. Because the molecular motor processes the nucleic acid, e.g., with turnover numbers in the range of tens-to-hundreds of bases per second, translocation can only occur at that rate, rather than 500,000 or more bases per second for nucleic acid translocation in the absence of a molecular motor. Molecular motor processing for nanopore sequencing at 50 Hz or higher is much faster (and less expensive) than current sequencing instruments.

In the present invention, the rate of movement of a polynucleotide with respect to a nanopore aperture may be between 0 and 2000 Hz, desirably between 50–1500 Hz, 100–1500 Hz, or 350–1500 Hz, e.g., at least 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, or 1900 Hz and/or at most 1750, 1500, 1450, 1400, 1350, 1300, 1250, 1200, 1150, 1100, 1050, 1000, 950, 900, 850, 800, 750, 700, 650, 600, 550, 500, 450, 400, 350, 300, 250, 200, or 150 Hz. Desirably, the rate is controlled by the use of a molecular motor that moves a polynucleotide at a substantially constant rate, at least for a portion of time during a characterization. In addition, the range of rate of movement may depend on the molecular motor. For example, for a RNA polymerase, a desirable range is 350–1500 Hz; for a DNA polymerase, a desirable range is 75–1500 Hz; and for ribosomes, helicases and exonucleases, a desirable range is 50–1500 Hz.

The intrinsic rate of movement of a particular molecular motor may be modified, e.g., by chemical modification of the motor, by changes in temperature, pH, ionic strength, the presence of necessary cofactors, substrates, inhibitors, agonists, or antagonists, by the nature of the medium (e.g., the presence of nonaqueous solvents or the viscosity), by external fields (e.g., electric or magnetic fields), and hydrodynamic pressure. Such modifications may be used to start, stop, increase, decrease, or stabilize the rate of movement, which may occur during a particular characterization. In addition, such modifications may be used as switches, brakes, or accelerators, e.g., to start, stop, increase, or decrease movement of a polynucleotide. In alternative embodiments, external forces (e.g., electric or magnetic fields or hydrodynamic pressure) generated other than by molecular motors may be used to control the rate of movement. The rate of movement may be substantially slowed or even stopped (e.g., paused) before, during, or after analysis of a particular polynucleotide.

Figure 8:
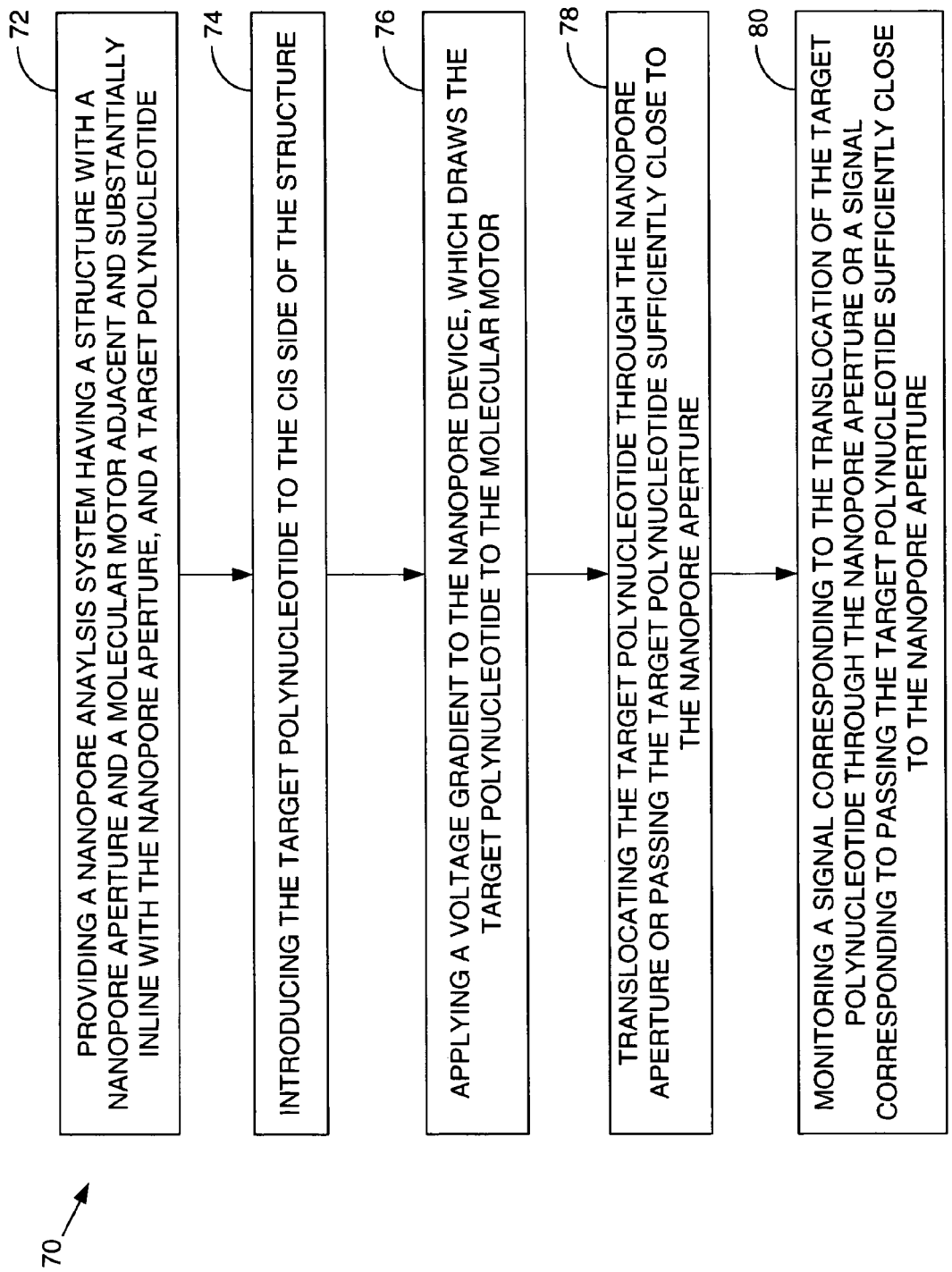
FIG. 8 is a flow diagram of a representative process for using a nanopore device.

FIG. 8 is a flow diagram illustrating a representative process 70 for using the nanopore device 12a . . . 12d of a nanopore analysis system 10. As shown in FIG. 8, the functionality (or method) may be construed as beginning at block 72, where a structure 22 with a nanopore aperture 24 and molecular motor 26 adjacent and substantially inline with the nanopore aperture 24, are provided. In block 74, a target polynucleotide is introduced to the cis side of the nanopore device 12a . . . 12d. In block, 76, the target molecule is allowed to either freely diffuse to the molecular motor or be actively drawn to the molecular motor, e.g., using a voltage gradient, applied to the nanopore device 12a . . . 12d. In block 78, the target polynucleotide is moved with respect to nanopore aperture 24. In block 80, a signal corresponding to the movement of the target polynucleotide is monitored by the nanopore detection system 14.

Figure 9A:
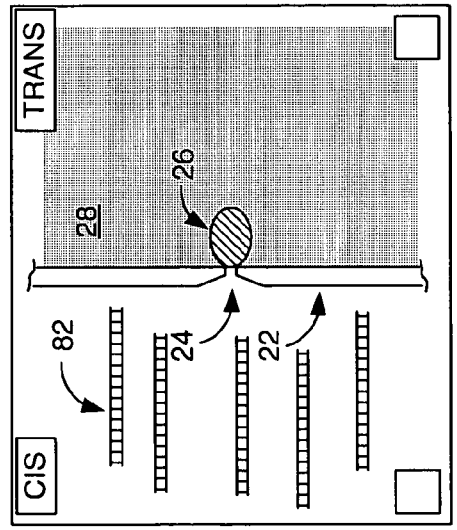
FIG. 9A through 9D are diagrams of a representative process for using a representative nanopore device having a molecular motor disposed on the trans side of the nanopore device.

FIG. 9A through 9D illustrate a representative process for using the nanopore analysis system 10. FIG. 9A illustrates a nanopore device 12a having the molecular motor 26 substantially immobilized on the trans side of the nanopore device 12a by a matrix material 28, while a plurality of target polynucleotides 82 are located on the cis side of the nanopore device 12a.

As discussed above, the nature of a molecular motor may require certain properties in the target polynucleotide. One skilled in the art would be able to prepare a sample for use with a particular molecular motor. For example, when the molecular motor 26 is a DNA polymerase, the target polynucleotide 82 may have a nick in the strand near one termini of the target polynucleotide 82, or a primer is present. Such primers may be based on random sequence, known sequences, or the addition of a known sequence to a target polynucleotide (e.g., the addition of a poly-A tail). In another embodiment, when the molecular motor 26 is a RNA polymerase, the target polynucleotide 82 may include a nascent RNA strand (e.g., 10 to 100 nucleotides in length). When RNA or DNA primers are employed, they may be hybridized to the target polynucleotide on the cis or trans side of the nanopore. In still another embodiment, when the molecular motor 26 is an exonuclease molecule, the target polynucleotide 82 may have a recessed 5'-phosphorylated terminus. In another example, when the molecular motor 26 is a helicase, the target polynucleotide 82 may not need any modifications.

Figure 9B:
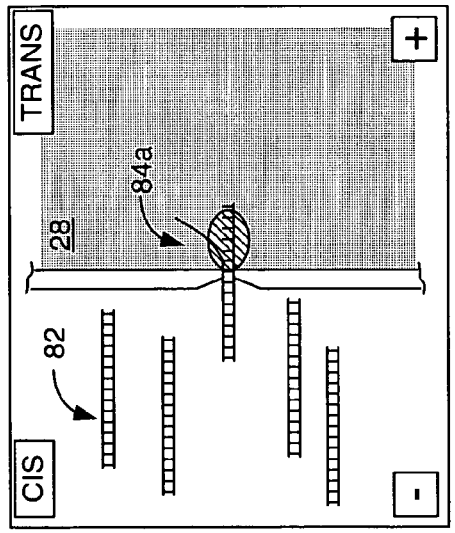

In FIG. 9B a voltage gradient is applied to the nanopore device 12a, which draws the target polynucleotide 82 to the cis side of the nanopore aperture 24, so that the target polynucleotide 82 engages the molecular motor 26 disposed on the trans side of the nanopore aperture 24. Once the target polynucleotide 82 engages the molecular motor 26, the voltage gradient may be reduced or turned off. For example, if the molecular motor 26 is a helicase, then the addition of an energy source (e.g. ATP; not shown) to the trans solution activates the helicase activity and draw double-stranded DNA target polynucleotide through the pore aperture 24 as the helicase separates the two strands of DNA. Although not shown in FIG. 9B, nucleotide triphosphates, or any other reagents required for molecular motor activity, can be added to the trans side of the nanopore device 12a, e.g., NTPs if the molecular motor 26 is a DNA polymerase. In this case, the double-stranded DNA is drawn through the pore as the polymerase catalyzes the step-wise addition of nucleotides to 3'-terminus of the nicked DNA, or single stranded DNA to which a primer is hybridized (either on the cis or trans side) is drawn through the pore. In alternative embodiments, the voltage gradient can be left on, but the polarity of the voltage gradient is changed so that it is the opposite of the initial voltage gradient, which creates an opposing force, or the magnitude of the voltage may be reduced The opposing force can be useful to control the rate of translocation of the target polynucleotide 82. Furthermore, an exonuclease or endonuclease can be added to the trans side of the nanopore device 12a to digest any translocated target polynucleotides.

Figure 9C:
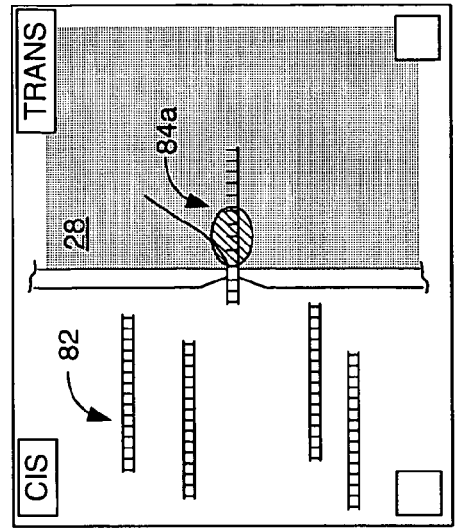
Figure 9D:
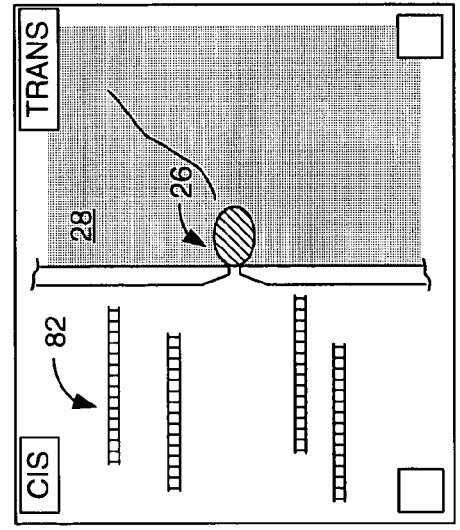

FIG. 9C illustrates the translocation of a target polynucleotide 82 through the nanopore aperture 24 by the molecular motor 26. A signal corresponding to the translocation of the target polynucleotide 82 through the nanopore aperture 24 is monitored by the nanopore detection system 14. FIG. 9D illustrates the complete translocation of the target polynucleotide 82 through the nanopore aperture 24. Once one target polynucleotide 82 is translocated through the nanopore aperture 24, a voltage bias can be applied to draw another target polynucleotide 82 to the nanopore aperture 24, and the process may continue as described above.

Figure 10B:
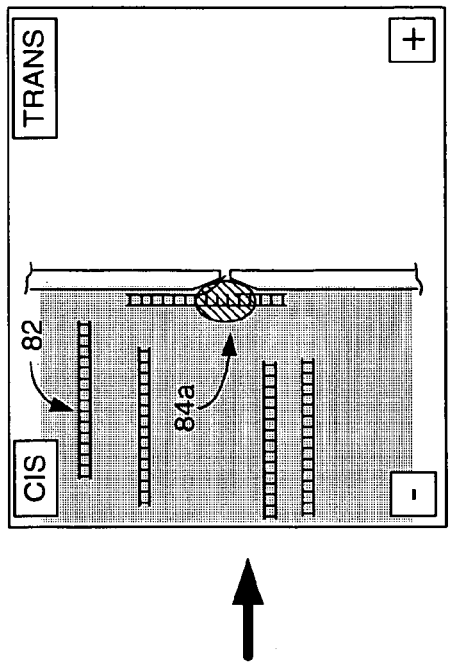
FIG. 10A through 10D are diagrams of a representative process for using a representative nanopore device having a molecular motor disposed on the trans side of the nanopore device.
Figure 10C:
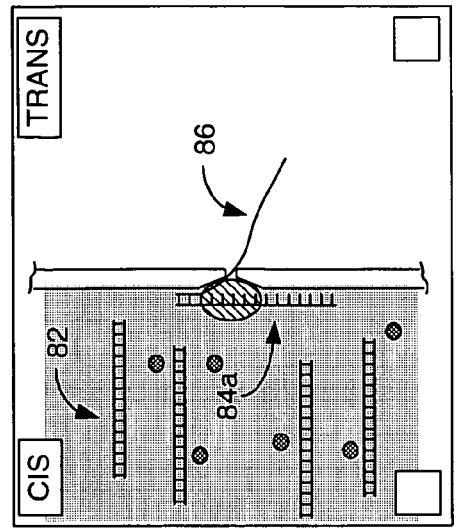
Figure 10A:
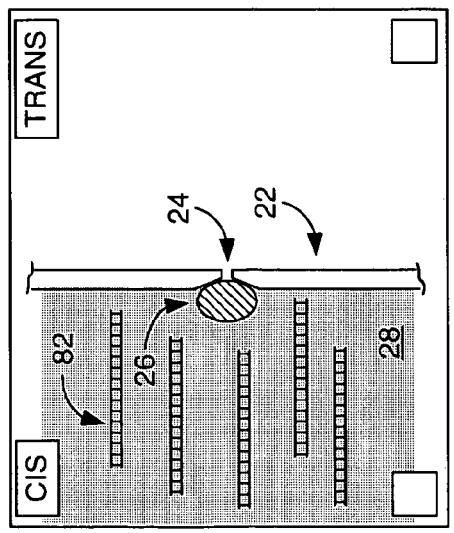

FIGS. 10A through 10D illustrate another representative process for using the nanopore analysis system 10. FIG. 10A illustrates a nanopore device 12b having the molecular motor 26 substantially immobilized on the cis side of the nanopore device 12b by a matrix material 28 and a plurality of target polynucleotides 82 are located on the cis side of the nanopore device 12b. As previously stated, the target polynucleotides 82, in some instances, may need to be modified to be analyzed using the nanopore analysis system 10.

FIG. 10B illustrates the nanopore device 12b having an applied voltage gradient, which draws the target polynucleotide 82 to the cis side of the nanopore aperture 24, so that the target polynucleotide 82 engages the molecular motor 26 disposed on the cis side of the nanopore aperture 24 to form a target polynucleotide/molecular motor complex 84a. Once the target polynucleotide 82 engages the molecular motor 26, the voltage gradient may be turned off or otherwise modified as described herein. In one example, the molecular motor 26 is a helicase, and the polynucleotide is double-stranded DNA. The addition of an energy source (e.g., ATP; not shown) to the cis solution activates the helicase to separate the DNA and may push one of the strands of the DNA through the pore aperture 24. In another example, the molecular motor 26 is a DNA polymerase, and the double-stranded DNA contains a nick. In this example, the strand that is dislodged as the polymerase acts may be analyzed, e.g., as it traverse the nanopore.

Figure 10D:
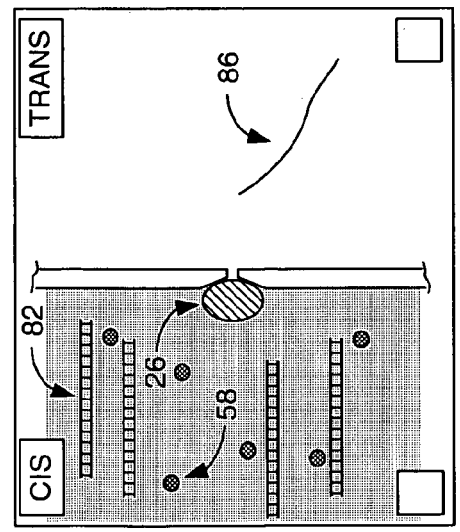

FIG. 10C illustrates the translocation of a single-strand of the target polynucleotide 86 through the nanopore aperture. A signal corresponding to the translocation of the single-strand of the target polynucleotide 86 through the nanopore aperture 24 is monitored by the nanopore detection system 14. FIG. 10D illustrates the complete translocation of the single-strand of the target polynucleotide 86 through the nanopore aperture 24. Once one single-strand of the target polynucleotide 86 is translocated through the nanopore aperture 24, a voltage gradient can be applied again to draw another target polynucleotide 82 to the nanopore aperture 24, and the process may continue as described above.

EXAMPLES

Example 1

E. coli Exonuclease I

Figure 11:
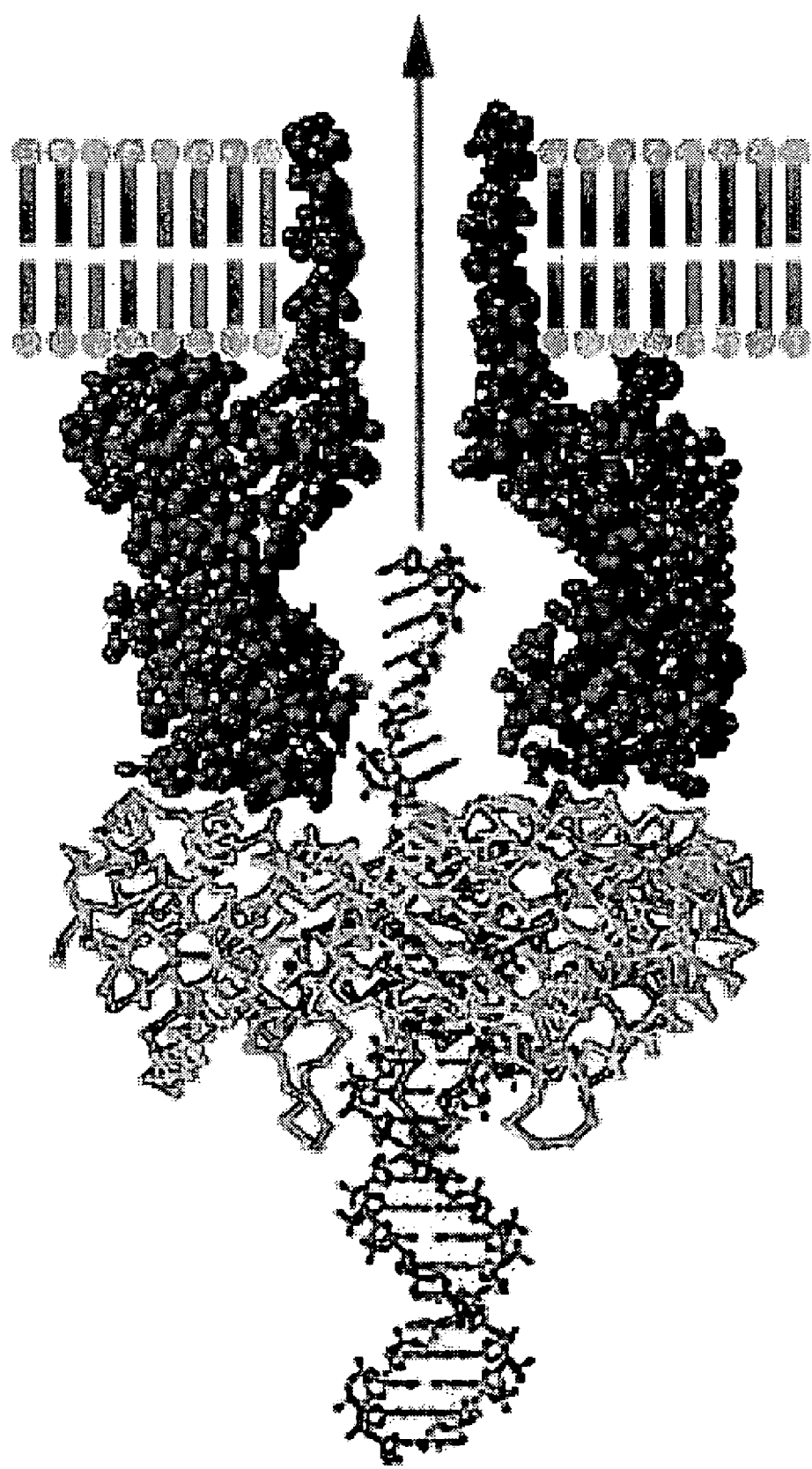
FIG. 11 is a schematic depiction of regulating DNA delivery into a nanoscale pore using a molecular motor as a brake. This schematic shows λ exonuclease digesting dsDNA and feeding the ssDNA product into an α-hemolysin pore. The applied electric field across the pore is required to capture the DNA/enzyme complex and then drive the ssDNA product sequentially through the detector. The schematic is to scale.

E. coli Exonuclease I catalyses digestion of single stranded DNA from 3' termini, releasing 5'-phosphorylated mononucleotides and leaving 10 nt or shorter fragments at completion. It functions as a monomer, forming a ring that binds to a 13 base sequence at the 3' ssDNA terminus (Brody Biochemistry 30:7072 (1991)). Binding is relatively weak (Km~1 µM) (Brody et al. J. Biol. Chem. 261:7136 (1986)), and ssDNA hydrolysis is inhibited by 3' phosphorylation. Processivity has been estimated to be >900 nt in bulk studies (Brody et al. J. Biol. Chem. 261:7136 (1986)). FIG. 11 shows DNA being moved through a nanopore by ExoI.

Figure 12:
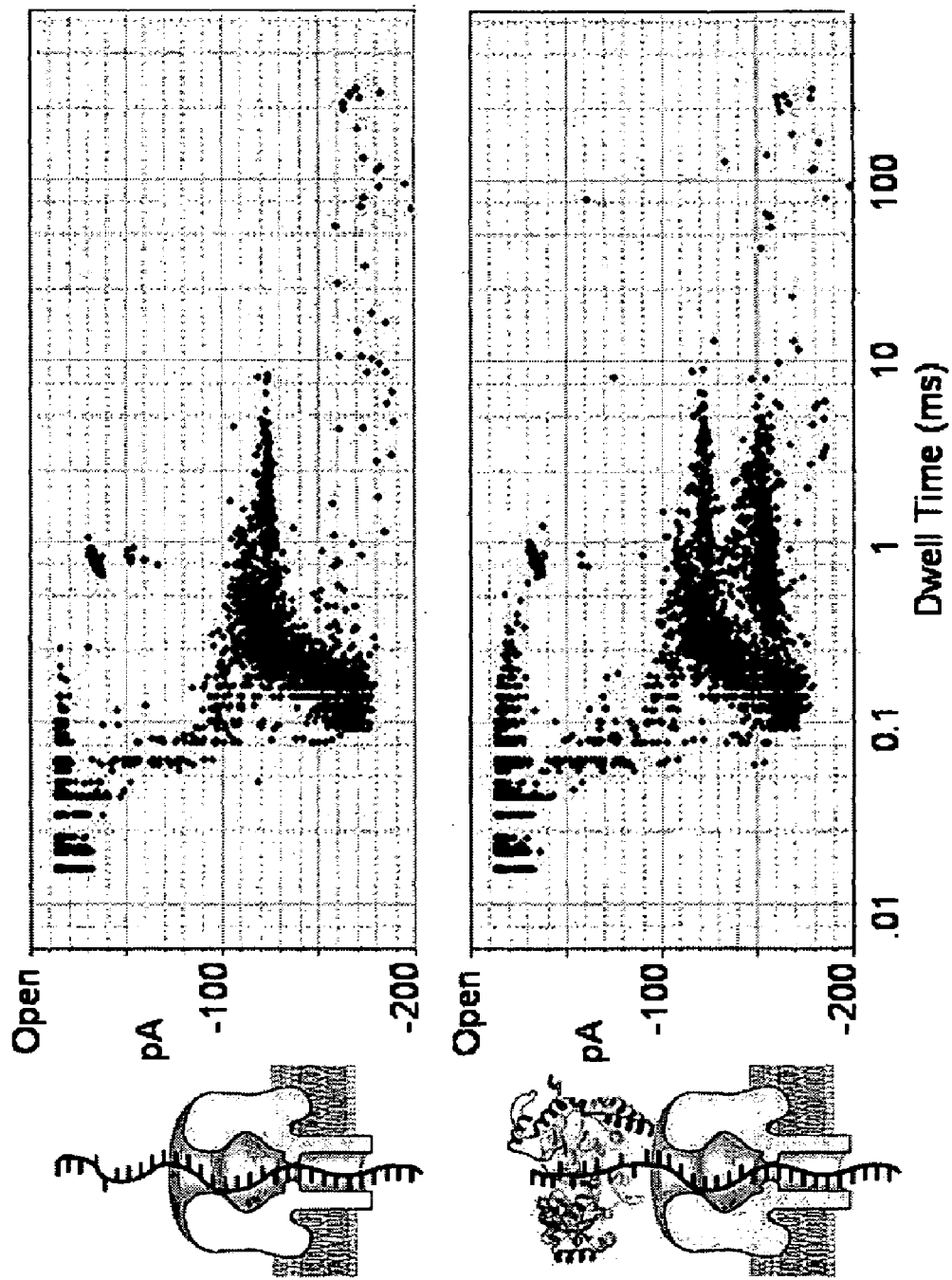
FIG. 12 is a schematic depiction and experimental data from binding of *E. coli* Exonuclease I to ssDNA 64mers. Molecules were captured by applying a 180 mV bias (trans side positive). The buffer used was 1M KCl, 10 mM HEPES(KOH) at pH 8.0 and 23° C. No $Mg^{2+}$ was present. Each point represents capture and translocation of one DNA molecule. The top graph shows results for 1 µM of a ssDNA 64 mer. The bottom graph shows the results following addition of 1 µM of Exo I.

FIG. 12 shows a nanopore experiment in which we examined a synthetic ssDNA 64mer (1 µM final concentration) before and after addition of 1 µM Exonuclease I (Solbrig et al. "DNA processing by lambda-exonuclease observed in real time using a single-ion channel." Biophysical Society, February, Baltimore, Md. (2004)). In the absence of the enzyme, a two dimensional event diagram (FIG. 12, top) revealed a pistol-shaped cluster of ssDNA translocation events. Blockade amplitudes were below –100 pA and dwell times in the pore ranged from ~0.1 to 10 ms, with an average duration of 0.2 ms. Upon addition of equimolar Exonuclease I in the presence of $Mg^{2+}$, which activates catalyzed hydrolysis, virtually all of the blockade events disappeared in several seconds, as expected (not shown). However, addition of Exonuclease I in the absence of $Mg^{2+}$ produced a new cluster of events (FIG. 12, bottom), centered at –160 pA and ranging from 0.2 to 9 ms, with an average duration of 2 ms. Consistent with earlier indirect biochemical measurements (Brody et al. J. Biol. Chem. 261:7136 (1986)), we found that the Kd's were ~1 $\mu M^{-1}$. This relatively weak binding affinity is also consistent with the small effect of the ExoI complex on translocation rate, i.e. a ten-fold reduction compared to ssDNA alone. This suggests that the Exonuclease I slowed the rate of translocation 10 fold, but, because the reduction in translocation rate was only 10 fold, it also suggests that the force applied to DNA by the field across the pore (~6 pN at 180 mV (Sauer-Budge et al. Phys. Rev. Lett. 90:238101 (2003); Mathe et al. Biophys J. 87:3205 (2004))) is strong enough to cause the nucleotide to slip through the enzyme, in effect momentarily or partially disrupting the normal enzyme-polynucleotide interaction. For this reason, Exonuclease I may not be ideal for controlling the rate of DNA movement.

Figure 13:
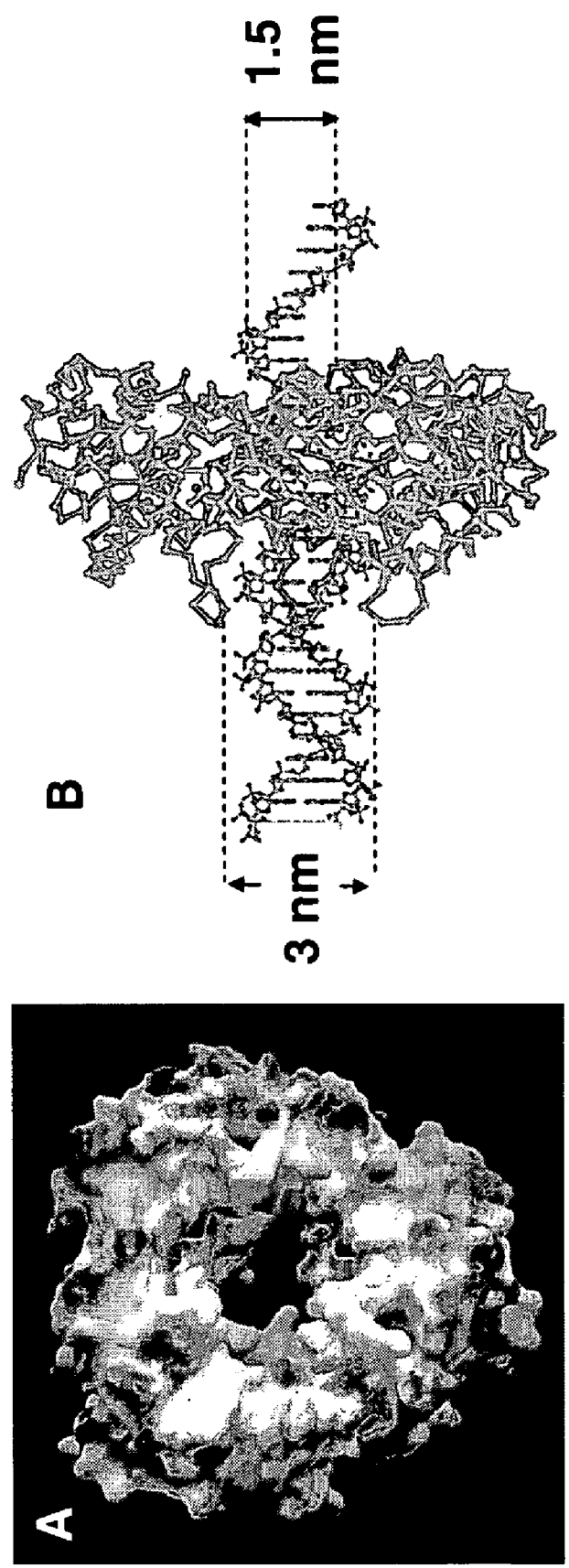
FIG. 13 is a schematic depiction of the structure of λ exonuclease from Kovall et al. Science 277:1824 (1997). A) Crystal structure of the homotrimer looking down through the pore which contains the catalytic domain that processively hydrolyzes nucleotides from one strand of dsDNA leaving one DNA strand intact. B) Schematic view of dsDNA entering the larger pore orifice and ssDNA exiting the smaller orifice.

Example 2

λ Exonuclease

λ exonuclease is a 24 kD protein encoded by phage λ. This enzyme strongly binds duplex DNA at 5' phosphorylated blunt- or 5'-recessed ends (Km~1 nM) (Mitsis et al. Nucl. Acid Res. 27:3057 (1999)), and digests one of the strands in the 5' to 3' orientation. Analysis of X-ray crystals (Kovall et al. Science 277:1824 (1997); Kovall et al. Proc. Natl. Acad. Sci. U.S.A. 95:7893 (1998)) revealed that the functional enzyme is a homotrimer which forms a toroidal structure with a hole in its center that tapers from 3.0 nm at one end to 1.5 nm at the other (FIG. 13). It is inferred that dsDNA enters the trimer complex through the 3 nm opening and that the intact single strand exits the opposite side via the 1.5 nm aperture. Recent single molecule studies indicate that the enzyme cuts at tens of nt $s^{-1}$ at room temperature (Perkins et al. Science 301:1914 (2003); van Oijen et al. Science 301:1235 (2003)). In vitro digestion of single dsDNA molecules is characterized by nearly constant speeds (4 nm $s^{-1}$) interspersed by pauses that can last for tens of seconds. Pausing is believed to be caused by sequence-specific interactions between the intact ssDNA strand and residues in the central channel of the enzyme (Perkins et al. Science 301:1914 (2003)). Recent single molecule studies reveal average processivity of 18,000±8000 bp (van Oijen et al. Science 301:1235 (2003)). $Mg^{2+}$ is the only essential cofactor for catalysis, and thus provides a useful "switch" for activating the enzyme. Comprehensive studies to examine the force dependence of λ exonuclease catalysis have not been published, but it is known that a force of 3 pN does not alter turnover rate (Perkins et al. Science 301:1914 (2003)).

Because the enzyme hydrolyzes only one strand of the DNA, a single stranded product results. We reasoned that the single strand product of the enzyme will be captured and extended in an electrical field (FIG. 11). The enzyme outside diameter (~8 nm) exceeds the dimensions of the pore vestibule inner diameter (2 nm), so it cannot enter the pore. Thus, in principle, the rate of DNA translocation will be regulated by the rate of single strand generation by the bound enzyme.

Experiments combining λ exonuclease with a model α-hemolysin pore confirm these predictions (Solbrig et al. "DNA processing by lambda-exonuclease observed in real time using a single-ion channel." Biophysical Society, February, Baltimore, Md. (2004)) and support the general utility of our approach. Briefly, individual α-hemolysin channels were established in 20 μm diameter lipid bilayers on a horizontal Teflon orifice. Buffer in the cis compartment was composed of 75 mM $MgCl_2$, 0.25M sucrose, 10 mM HEPES/KOH at pH 8.0. This buffer was a compromise between the high salt concentration (1.0 M KCl) that is optimal for α-hemolysin pore stability, and the poor tolerance of λ exonuclease to high monovalent salt concentrations. The voltage regime (+200 mV, trans side positive for 450 ms) allowed capture and examination of a DNA molecule as it translocated through the nanopore. This was followed by −160 mV (trans side negative) which expelled any DNA molecules that were not translocated during the 450 ms capture and translocation phase. Data were digitally recorded at 50 kHz following analog filtering at 10 kHz using a low-pass Bessel filter.

Figure 14:
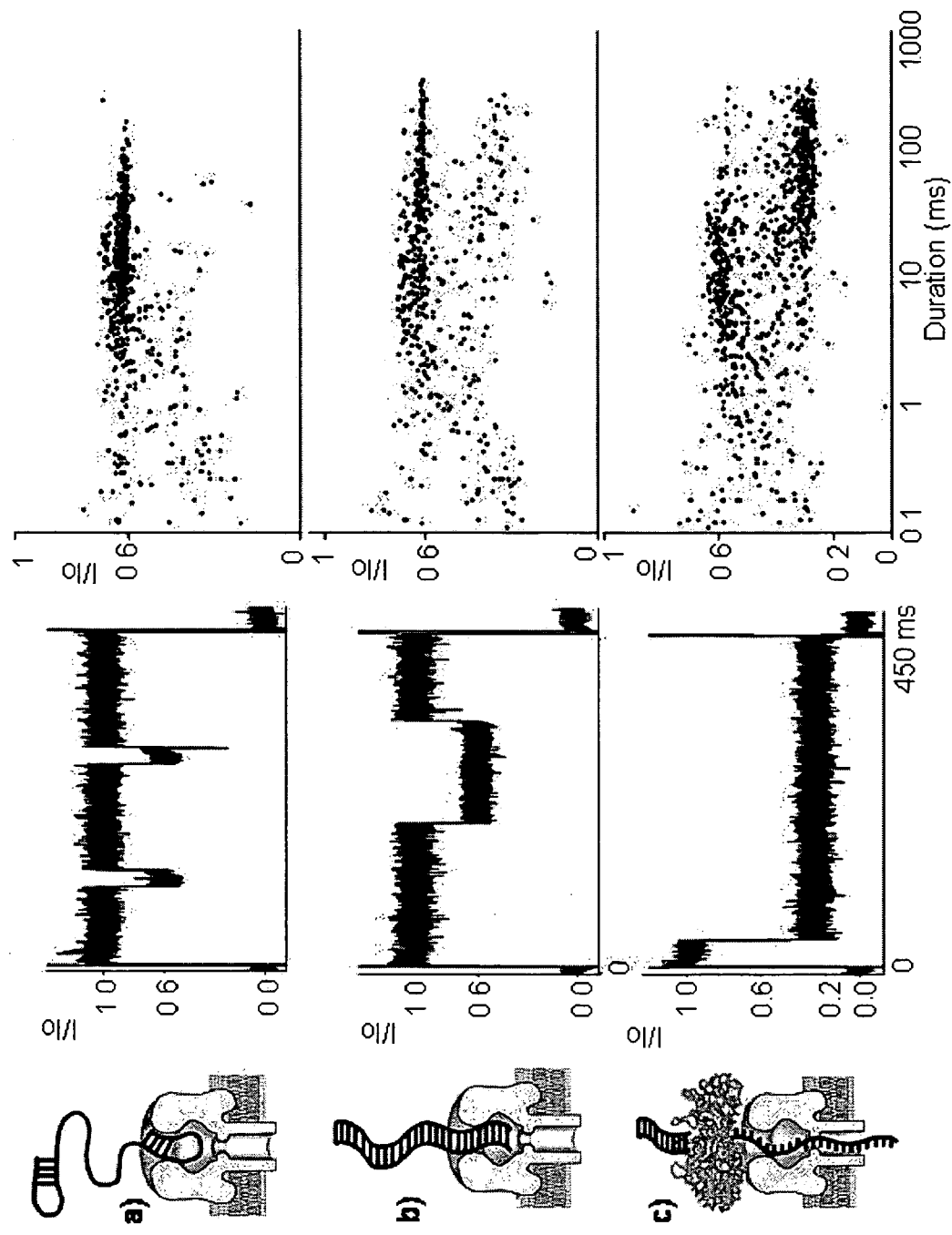
FIG. 14A–14C are graphs showing the capture of dsDNA molecules bound to λ exonuclease. A) Events caused by capture of ssDNA 60 mers at 5 µM. B) Events caused by annealing of a ssDNA complement to the original ssDNA 60 mer for 15 minutes. C) Events seen after exonuclease (2.5 µM λ) addition to the dsDNA formed in B).
Figure 15:
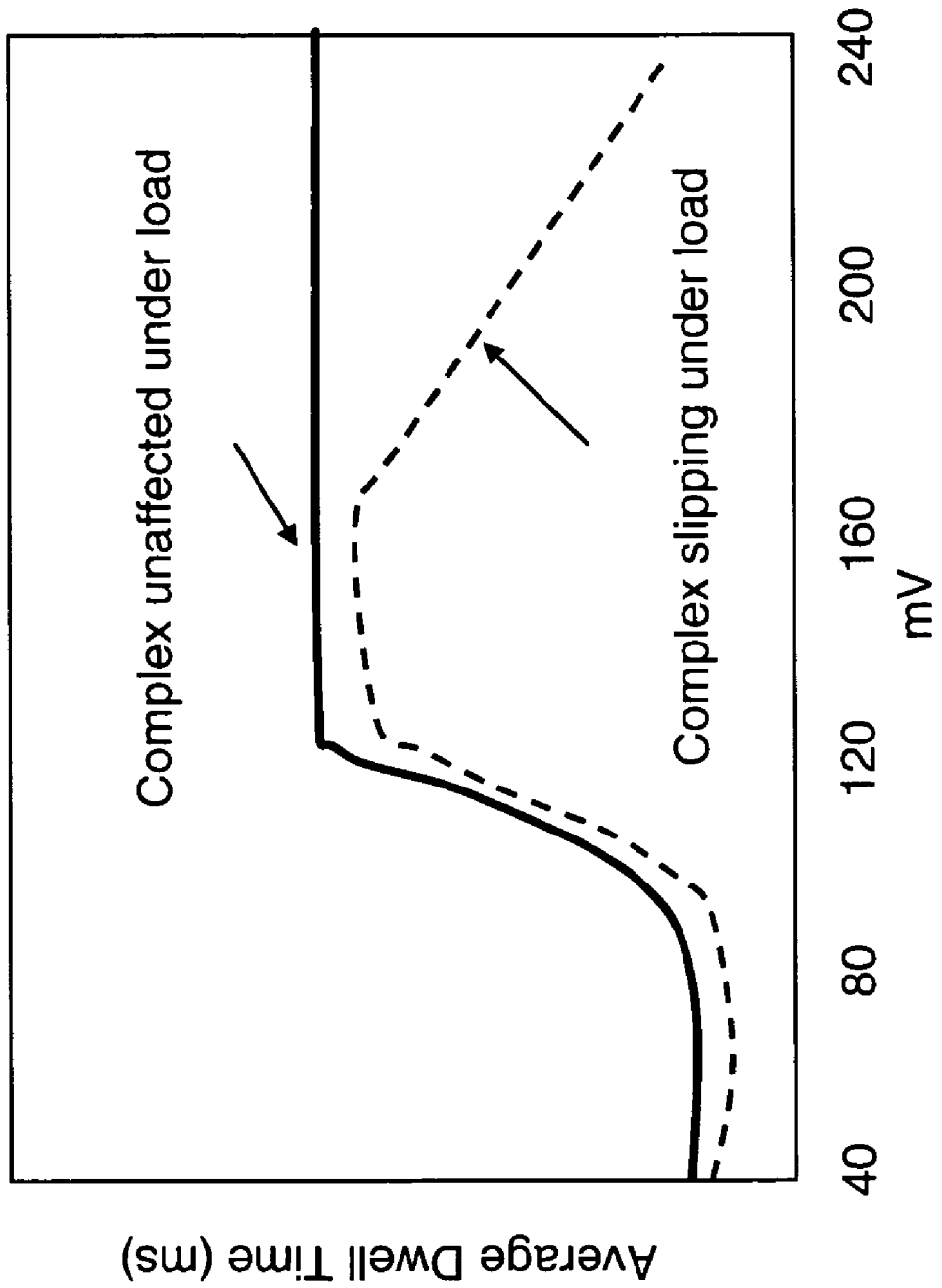
FIG. 15 is graph showing the anticipated effect of load on dwell time of the λ exonuclease/dsDNA complex absent $Mg^{2+}$.

When no DNA was added to the cis compartment, there were no recorded events during the 100 second duration of the experiment (data not shown). Subsequent addition of a ssDNA 60mer at 5 μM on the cis side caused thousands of events typified by those shown in FIG. 14a (center), and summarized in the two dimensional plot (FIG. 14a, right). The dominant cluster at I/Io=0.6 is due to ssDNA hairpins that form at either end of this construct, which is a standard duplex used in λ exonuclease research (Mitsis et al. Nucl. Acid Res. 27:3057 (1999)). We next added 5 μM of a ssDNA 60mer reverse complement to the original oligonucleotide and allowed annealing for 15 minutes. A typical blockade event is shown in FIG. 14b (center). Note that the duration of events at I/Io=0.6 (FIG. 14b right) is right-shifted relative to the ssDNA events in FIG. 14a, and a new dispersed cluster of events has emerged at approximately I/Io=0.35 with durations in excess of 10 ms. These two classes of events do not occur in the absence of dsDNA, and we infer that these are the signatures of dsDNA lacking bound enzyme. We next added λ exonuclease at a monomer concentration of ~2.5 μM. Following 20 minutes of binding and digestion, the two dimensional plot of events was dominated by a leftward shift of events at I/Io=0.6 consistent with enzymatic conversion of dsDNA to ssDNA and dissociation of the homotrimer from the DNA substrate. This was accompanied by a cluster of blockades at I/Io=0.25 (FIG. 14c, right), consistent with enzymatic conversion of dsDNA to ssDNA that is captured in the pore while bound to the enzyme (FIG. 14c, left). When single stranded 60mer controls (not shown) without hairpins are translocated through this nanopore, $I/I_O \cong 0.25$ and the duration of translocation is <0.2 ms (Meller et al. Proc. Natl. Acad. Sci. USA 97:1079 (2000)). Thus, the class of events centered on $I/I_O=0.25$ with durations of >10 ms are consistent with ssDNA that is slowly translocating through the nanopore under the control of λ-exonuclease digestion. We note that some of these events must also correspond to DNA/enzyme complexes that are indefinitely paused for reasons that we do not yet fully understand.

OTHER EMBODIMENTS

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the appended claims.

Other embodiments are in the claims.

The invention claimed is:

1. A nanopore analysis system, comprising:
   (a) a structure having a nanopore aperture; and
   (b) a molecular motor adjacent the nanopore aperture, wherein the molecular motor is capable of moving a polynucleotide with respect to the nanopore aperture at a rate of 350–2000 Hz.

2. The nanopore analysis system of claim 1, wherein the molecular motor is substantially immobilized inline with the nanopore aperture by a gel matrix.

3. The nanopore analysis system of claim 2, wherein the molecular motor is covalently bonded to the gel matrix.

4. The nanopore analysis system of claim 1, wherein the molecular motor comprises a DNA polymerase, a RNA polymerase, a ribosome, an exonuclease, or a helicase.

5. A nanopore analysis system, comprising:
   (c) a structure having a nanopore aperture; and
   (d) a molecular motor (i) comprising a DNA polymerase, a ribosome, an exonuclease, or a helicase and (ii) disposed adjacent the nanopore aperture, wherein the molecular motor is capable of moving a polynucleotide with respect to the nanopore aperture at a rate of 75–2000 Hz.

* * * * *